(12) United States Patent
Suenaga et al.

(10) Patent No.: US 9,388,376 B2
(45) Date of Patent: Jul. 12, 2016

(54) METHOD FOR COUNTING SUBJECT MATTERS TO BE COUNTED IN CONTAINER

(71) Applicants: Ryo Suenaga, Yokohama (JP); Yoichi Ishizaki, Yokohama (JP); Satoshi Tanaka, Yokohama (JP); Takahiko Totani, Yokohama (JP); Kyohei Ota, Yokohama (JP)

(72) Inventors: Ryo Suenaga, Yokohama (JP); Yoichi Ishizaki, Yokohama (JP); Satoshi Tanaka, Yokohama (JP); Takahiko Totani, Yokohama (JP); Kyohei Ota, Yokohama (JP)

(73) Assignee: TOYO SEIKAN KAISHA, LTD., Tokyo (JP)

( * ) Notice: Subject to any disclaimer, the term of this patent is extended or adjusted under 35 U.S.C. 154(b) by 263 days.

(21) Appl. No.: 14/023,575

(22) Filed: Sep. 11, 2013

(65) Prior Publication Data

US 2014/0011186 A1    Jan. 9, 2014

Related U.S. Application Data

(62) Division of application No. 13/138,589, filed as application No. PCT/JP2010/001414 on Mar. 2, 2010.

(30) Foreign Application Priority Data

Mar. 9, 2009   (JP) .................................. 2009-055651
Oct. 21, 2009   (JP) .................................. 2009-242826

(51) Int. Cl.
C12M 1/34 (2006.01)
C12M 1/26 (2006.01)
C12M 1/00 (2006.01)
C12M 1/06 (2006.01)

(52) U.S. Cl.
CPC ............... *C12M 41/40* (2013.01); *C12M 23/14* (2013.01); *C12M 23/34* (2013.01); *C12M 27/02* (2013.01); *C12M 33/18* (2013.01); *C12M 41/36* (2013.01)

(58) Field of Classification Search
CPC ...... C12M 41/40; C12M 33/18; C12M 23/34; C12M 41/36; C12M 23/14; C12M 27/02
See application file for complete search history.

(56) References Cited

U.S. PATENT DOCUMENTS

| | | |
|---|---|---|
| 3,850,748 A | 11/1974 | Cook et al. |
| 5,057,429 A | 10/1991 | Watanabe et al. |
| 5,572,321 A | 11/1996 | Pinier et al. |
| 6,602,711 B1 | 8/2003 | Thomson et al. |
| 2003/0003527 A1 | 1/2003 | Shimakita et al. |
| 2007/0048859 A1 | 3/2007 | Sears |
| 2007/0128716 A1 | 6/2007 | Wang et al. |

(Continued)

FOREIGN PATENT DOCUMENTS

| | | |
|---|---|---|
| EP | 1256624 A1 | 11/2002 |
| JP | S64-018433 A | 1/1989 |

(Continued)

OTHER PUBLICATIONS

Europe Patent Office, "Search Report for EP 14163506.0," Sep. 1, 2014.

(Continued)

*Primary Examiner* — Taeyoon Kim
(74) *Attorney, Agent, or Firm* — Manabu Kanesaka

(57) ABSTRACT

A method for counting counted targets disposed in a liquid enclosed in a container, includes adjusting a thickness of at least a part of the container; setting at least a part of the adjusted part as a measurement target region; and counting a number of counted targets in the measurement target region.

7 Claims, 22 Drawing Sheets

(56) References Cited

U.S. PATENT DOCUMENTS

| | | |
|---|---|---|
| 2008/0019952 A1 | 1/2008 | Kolossov et al. |
| 2009/0111179 A1 | 4/2009 | Hata et al. |
| 2010/0112691 A1 | 5/2010 | Green et al. |

FOREIGN PATENT DOCUMENTS

| | | |
|---|---|---|
| JP | H03-007575 A | 1/1991 |
| JP | H07-079772 A | 3/1995 |
| JP | H08-43292 A | 2/1996 |
| JP | 2000-125848 A | 5/2000 |
| JP | 2006-325437 A | 12/2006 |
| JP | 2009-505660 A | 2/2009 |
| WO | 00/66706 A1 | 11/2000 |
| WO | 2008/136371 A1 | 11/2008 |

OTHER PUBLICATIONS

European Patent Office, "Extended European Search Report for EP 10 75 0507", Aug. 22, 2013.

Japan Patent Office, "Office Action for JP 2009-242826," Mar. 18, 2014.

Japan Patent Office, Office Action for Japanese Patent Application No. 2010-45245, May 17, 2016.

(A) Before adjustment of thickness (B) After adjustment of thickness (1) Basic positions (2) Agitating state (3) Thickness-adjusting and precipitation-waiting state
(the case where the thickness is reduced)

(4) Microscope observation state (5) Thickness-adjusting and precipitation-waiting state
(the case where the thickness is increased)

| | | Moving speed V(mm/s) | | |
|---|---|---|---|---|
| | | 2.5 | 12.5 | 50 |
| Pressing degree | 2 | △ | △ | ○ |
| | 4 | △ | ○ | ○ |
| | 6 | ○ | ○ | ◎ |
| | 8 | ○ | ◎ | × |

△ : All the cells descended ··· Weak agitation
○ : Most of the cells descended ⎫
◎ : Most of the cells floated ⎬ ··· Medium agitation
× : All the cells floated ··· Strong agitation (Example 1) Thickness: 2.8 mm  Stationary time after agitation: 12 min.

(Comparative example 1) No pressing Thickness: approximately 16 mm  Stationary time after agitation: 60 min.

FIG.21

| | Comparative example 1 | Example 1 |
|---|---|---|
| Bag thickness (mm) | Approximately 16 (No pressing, the upper surface of the bag in a waveform) | 3.1 |
| Liquid thickness (mm) Bag thickness – upper and lower film thickness | — | 2.8 |
| The number of cells in the observation region | Counting impossible | 518 |
| Density ($\times 10^4$ cells/ml) | — | 74.00 |
| Actual measurement density ($\times 10^4$ cells/ml) | 69.1 | |
| Actual measurement value ratio | — | 1.07 |

(Example 3) Thickness: 6.7 mm 30 min.

(Example 5) Thickness: 2.8 mm 12 min.

(Example 2) Thickness: 10.7 mm Stationary time after agitation: 45 min.

(Example 4) Thickness: 3.7 mm 12 min.

FIG. 23

| | Example 2 | Example 3 | Example 4 | Example 5 |
|---|---|---|---|---|
| Bag thickness (mm) | 11.0 | 7.0 | 4.0 | 3.1 |
| Liquid thickness (mm) | 10.7 | 6.7 | 3.7 | 2.8 |
| The number of cells in the observation region | 718 | 519 | 245 | 189 |
| Density ($\times 10^4$ cells/ml) | 26.8 | 30.99 | 26.49 | 26.29 |
| Actual measurement density($\times 10^4$ cells/ml) | 27.33 | | | |
| Actual measurement value ratio | 0.98 | 1.13 | 0.97 | 0.96 |

METHOD FOR COUNTING SUBJECT MATTERS TO BE COUNTED IN CONTAINER

CROSS-REFERENCE TO RELATED APPLICATIONS

The present application is a divisional of U.S. Ser. No. 13/138,589 filed on Sep. 8, 2011. The application claims priority to Japanese patent application No. 2009-055651 filed on Mar. 9, 2009 and No. 2009-242826 filed on Oct. 21, 2009, which are incorporated by reference in its entirety.

TECHNICAL FIELD

The present invention relates to a method for counting subject matters to be counted disposed in a liquid enclosed in a container.

BACKGROUND ART

In recent years, demands exist for efficient large-scale cell culturing, tissues, and microorganisms under artificial environments, in fields such as pharmaceutical manufacturing, gene therapy, regenerative medical therapy, and immunotherapy.

In such large-scale cell culturing, especially regarding culturing of floating cells, agitation culturing is commonly practiced using culture vessels equipped with agitating blades. However, agitating blades are not used with cells subject to damage from external force or cells that proliferate while forming aggregates. Instead, a widely employed method is to enclose cells in a culture container where the cells are cultured while being kept stationary (with the cells down at the bottom). Then, in accordance with the degree of proliferation of the cells, the method involves transfer to another culture container with a larger bottom area or increasing the number of containers. Unfortunately, the stationary culturing is problematic in that as the aggregates of cells grow larger with the proliferation of cells, this causes a gradual deficiency of oxygen and nutrients to be fed to the cells, leading to degraded proliferation efficiency.

Additionally, although the transfer to another container involves agitation of a culture solution to cancel the unevenness of oxygen and nutrients, another problem arises in that the handling during the transfer causes damage to the cells, leading to degraded proliferation efficiency.

Meanwhile, shaking culture is also widely practiced to constantly agitate the culture container.

For example, patent document 1 describes a cell culturing apparatus that uses various patterns, such as rotation and shaking, to move a base on which a culture container is placed, thereby agitating a culture solution in the culture container.

Patent document 2 and patent document 3 describe cell culturing apparatuses that shake a liquid culture medium in a culture container while ensuring that no air bubbles occur, and that supply oxygen by motion of waves while ensuring that the cells are not damaged.

With the method of shaking by the cell culturing apparatuses, the entire culture medium is intensely agitated. This causes the cells to be separated from each other and the oxygen and nutrients to be dispersed in the whole area, so that the oxygen and nutrients are supplied sufficiently to each cell.

Additionally, such cell culturing requires the density of cells in the culture solution to be maintained within an appropriate range in accordance with the proliferation of the cells.

That is, an excessively high density of cells in the culture solution prevents a sufficient supply of oxygen and nutrients to each cell, leading to degraded cell proliferation efficiency. Likewise, an excessively low density of cells in the culture solution prevents sufficient securement of cell proliferation efficiency.

In view of this, cell culturing requires a grasp of the density of cells during culturing, by appropriately counting the number of cells in a culture solution in a culture container.

For example, patent document 4 discloses a cell culturing apparatus that properly maintains the density of cells in a culture solution in accordance with the proliferation of cells.

In order to measure the number of cells with such cell culturing apparatus, it is conventional practice to: sample a culture solution containing cultured cells through a sampling port coupled to the interior of the culture container; add a predetermined buffer solution to the sampled culture solution so as to adjust the density of the cells in the sampled culture solution to an appropriate density for measurement; and inject the resulting culture solution into a counter board that indicates the number of the cells. The number of the cells is read by an operator or a machine to calculate the density of the cells.

Patent document 5 discloses a culture apparatus equipped with photographing means. According to this culture apparatus, cell images are captured periodically and stored.

RELATED ART DOCUMENTS

Patent Documents

[Patent document 1] U.S. Pat. No. 5,057,429.
[Patent document 2] WO2000/66706.
[Patent document 3] Japanese Translation of PCT International Application Publication No. JP2007-511231.
[Patent document 4] WO2008/136371.
[Patent document 5] WO2007/052718.

SUMMARY OF THE INVENTION

Problems to be Solved by the Invention

Unfortunately, some kinds of cells have difficulty in cell proliferation if they are separated into individual cells. These kinds of cells improve their proliferation efficiency when they adhere in the form of aggregates of appropriate sizes. Specific examples include adhesive cells such as neural stem cells, embryonic stem cells, hepatic cells, cornea stem cells, pancreatic islet cells, and floating cells such as leukocyte cells.

With these cells, since the conventional stationary culturing involves intense agitation of the culture container at the time of every transfer, a problem arises in that the cells are separated from each other at the time of every agitation, leading to degraded cell proliferation efficiency.

Likewise, the shaking culture with the cell culturing apparatuses described in patent documents 1 to 3 involves intense agitation of the entire culture medium, turning the cells into an individually floating state in the culture medium. This makes the cells difficult to form into aggregates of appropriate sizes, to the detriment of the optimization of cell proliferation efficiency.

Additionally, counting the number of cells in a culture solution with the cell culturing apparatus described in patent document 4 requires sampling of the culture solution from the interior of the culture container. This involves disassembly of a culture system at the risk of contamination.

Additionally, the culture apparatus described in patent document 5, though capable of acquiring cell images, finds it difficult to measure the number of cells accurately based on the images and to obtain the density of the cells.

Specifically, when the cells in the culture container are photographed by the photographing means described in patent document 5, the number of the cells in the cell image is measured, and the number is divided by the volume of a part of the culture solution defined within the view field of the photographing means. Thus, the density of the cells is calculated.

However, with such direct observation of the cells in the cell container, when the density of the cells is so large that the cells overlap with each other as shown in FIG. 24, the number of the cells cannot be measured accurately. Meanwhile, when the density of the cells is excessively small, it is difficult to prospect the entire density, creating a problem of poor accuracy of the calculated cell density.

A comparison of the use of the photographing means in directly measuring the cells in a culture container with the use of the conventional counter board in actual measurement shows that the thickness of the counter board is usually approximately 0.1 mm, whereas the thickness of the culture container is approximately 1 to 2 cm, which is 100 to 200 times the thickness of the conventional counter board.

This means that the number of cells observed through the photographing means is 100 to 200 times larger than the number of cells actually measured by the counter board, when the respective volume densities are the same. Accordingly, the cells in the culture container oftentimes overlap with each other, and it is difficult to measure the number of cells by directly observing the cells in the culture container.

In view of this, the inventors have conducted an extensive study, and as a result, successfully obtained a cell density close to an actually measured value by: adjusting the thickness of a culture container to set the number of cells observed through the photographing means at a measurable number; and then measuring the number of the cells in the culture container by direct observation.

The present invention has been made in view of the above-described circumstances, and it is an object of the present invention to provide a method for counting subject matters to be counted in a container, by which the number of cells is measured in any density range in a culturing environment without disassembly of the culture system and irrespective of the density of proliferated cells.

Means of Solving the Problems

In order to achieve the above-described objects, according to one aspect of the present invention, a method for culturing cells using a culture container includes applying an external force to the culture container to carry out at least one of cell aggregate formation control and cell aggregate disintegration control with respect to cells in the culture container.

According to another aspect of the present invention, a cell culturing apparatus is to culture cells using a culture container. The cell culturing apparatus includes a loading base on which the culture container is placed, and an agitating member configured to press the culture container to a predetermined pressing degree and movable at a predetermined speed in a horizontal direction. The agitating member is configured to move to apply an external force to the culture container so as to control at least one of cell aggregate formation and cell aggregate disintegration with respect to the cells in the culture container.

According to another aspect of the present invention, a method for counting counted targets disposed in a liquid enclosed in a container includes adjusting a thickness of at least a part of the container. At least a part of the adjusted part is set as a measurement target region. A number of counted targets in the measurement target region is counted.

In the method for counting counted targets disposed in a liquid enclosed in a container, the liquid in the container is agitated to equalize the counted targets in the liquid prior to adjusting the thickness of at least a part of the container.

According to the other aspect of the present invention, a counting apparatus is to count counted targets disposed in a liquid enclosed in a container. The counting apparatus includes a loading base on which the container is placed, and an adjusting member configured to adjust at least a part of the container including a measurement target region to a predetermined thickness.

The counting apparatus may further include an agitating member configured to agitate the liquid in the container before the adjusting member adjusts the thickness of the container.

The counting apparatus may further include photographing means, counting means, and a driving device. The photographing means is for photographing counted targets disposed in the container. The counting means is for counting a number of the counted targets in a photographed image. The driving device is configured to, when the number of the counted targets is outside a predetermined range following the counting by the counting means, drive the adjusting member to adjust at least a part of the container to a predetermined thickness so as to render the number of the counted targets in the image within the predetermined range.

Advantageous Effects of the Invention

With the embodiments of the present invention, aggregates are adjusted to appropriate sizes during cell culturing of cells, tissues, and microorganisms, thereby improving cell proliferation efficiency.

Also with the embodiments of the present invention, the number of cells is counted without disassembly of a culture system and irrespective of the density of proliferated cells.

BRIEF DESCRIPTION OF THE DRAWINGS

FIG. 21 is a diagram showing results in example 1 of the present invention and comparative example 1.

FIG. 23 is a diagram showing results in examples 2 to 5 of the present invention.

BEST MODE FOR CARRYING OUT THE INVENTION

Description will be given below with respect to preferable embodiments of the method for culturing cells and cell culturing apparatus according to the present invention by referring to the accompanying drawings.

[First Embodiment]

Figure 1:
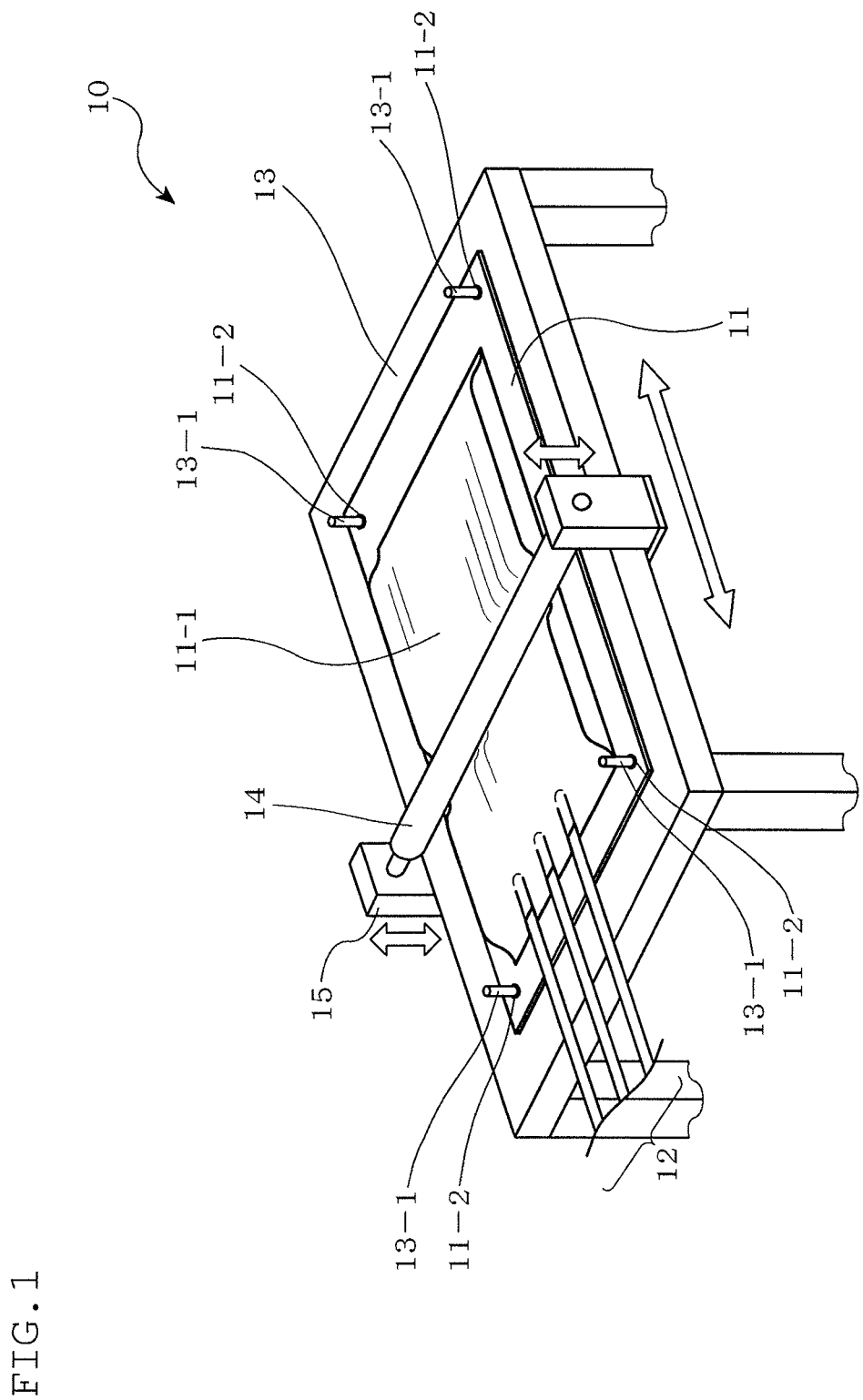
FIG. 1 is a diagram illustrating a cell culturing apparatus according to a first embodiment of the present invention.
Figure 2:
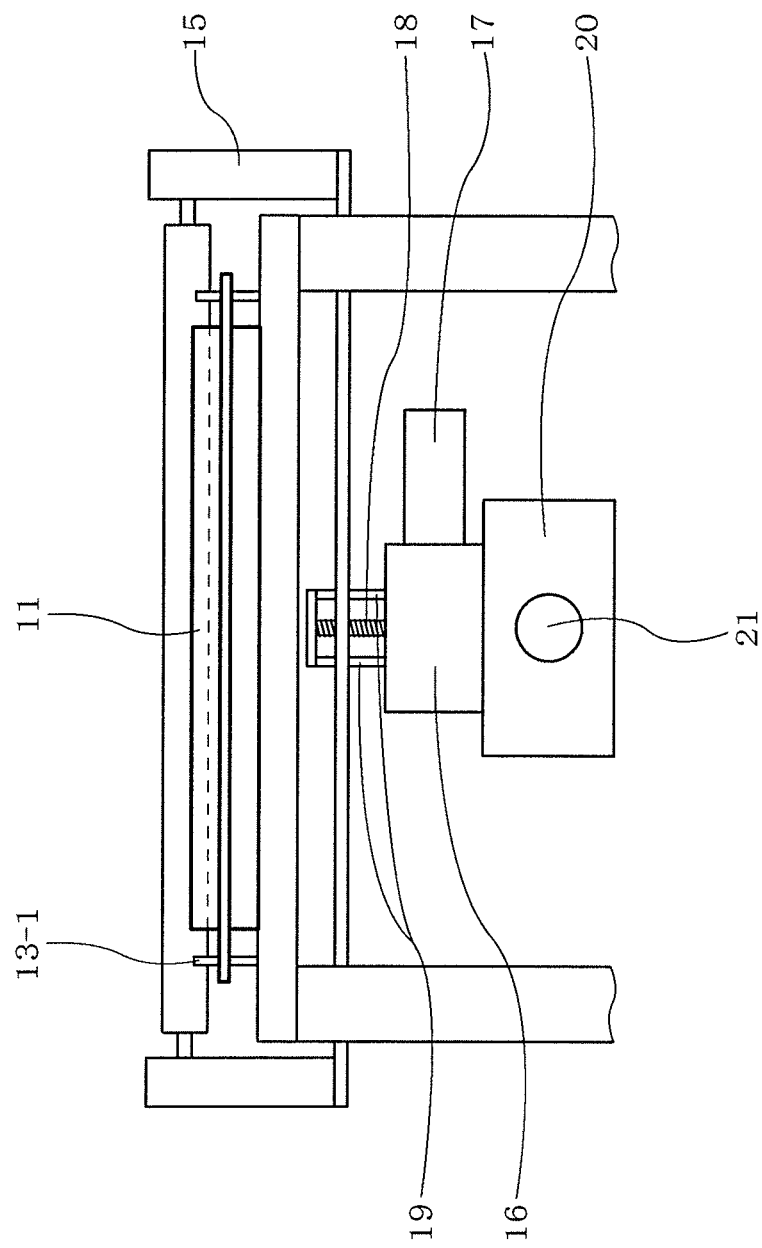
FIG. 2 is a diagram illustrating a driving device of the cell culturing apparatus according to the first embodiment of the present invention.
Figure 3:
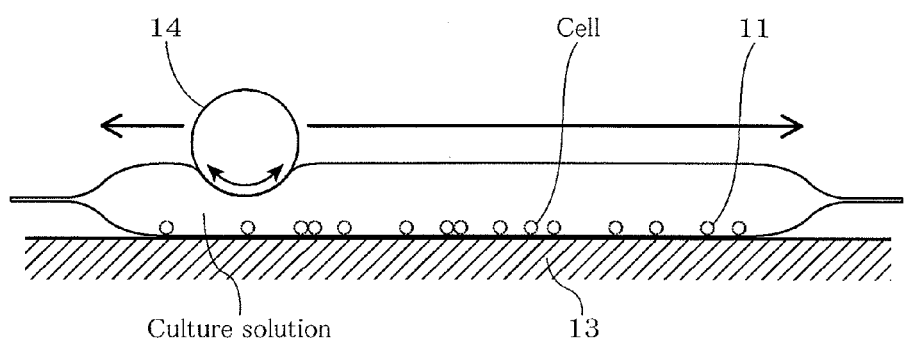
FIG. 3 is a schematic side view of the cell culturing apparatus according to the first embodiment of the present invention.
Figure 4:
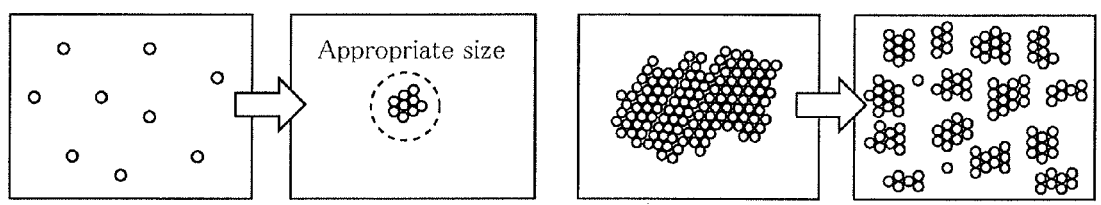
FIG. 4 is a diagram illustrating formation of an aggregate of cells and disintegration of the aggregate of the cells in the present invention.

First, referring to FIG. 1 through FIG. 4, a first embodiment of the present invention will be described. FIG. 1 is a diagram illustrating the cell culturing apparatus according to this embodiment. FIG. 2 is a diagram illustrating a driving device of the cell culturing apparatus according to this embodiment. FIG. 3 is a schematic side view of the cell culturing apparatus according to this embodiment. FIG. 4 is a diagram illustrating formation of an aggregate of cells and disintegration of the aggregate of cells in the present invention.

[Cell Culturing Apparatus 10]

As shown in FIG. 1, a cell culturing apparatus 10 according to this embodiment includes a culture container 11, a loading base 13, and an agitating member 14. A culture solution (culture medium) and cells are enclosed within a storage 11-1 of the culture container 11, and tubes 12 are coupled to the storage 11-1.

The culture container 11 is a container that is made of a soft packing material shaped in the form of a bag (bag type). The soft packing material used as the material of the culture container 11 provides the culture container 11 with flexibility and plasticity. Examples of the soft packing material include materials disclosed in JP2002-255277A ("FOOD PACKAGE USING SOFT PACKAGING FILM SHEET AND FOOD TAKING-OUT METHOD") and JP2004-323077A ("PRESSURIZEDLY SPOUTING BAG-SHAPED CONTAINER").

Also the culture container 11 has gas permeability required for cell culturing, and partially or entirely has transparency to permit confirmation of the contents. Examples of the material of the culture container satisfying the these conditions include polyolefins, ethylene-vinyl acetate copolymers, styrene elastomers, polyester thermoplastic elastomers, silicone thermoplastic elastomers, and silicone rubber.

The tubes 12 are used to inject a culture solution and cells into the culture container 11 from outside the culture container 11, and to collect them to outside the culture container 11. Although each of the four sides of the culture container 11 is sealed, at least two tubes 12 are coupled to the culture container 11. One of the at least two tubes 12 is used to inject cultured cells and a culture medium into the culture container 11 from outside the culture container 11, while the other tube is used to collect cultured cells and the culture medium out of the culture container 11. When three tubes 12 are attached as shown in FIG. 1, the third tube is used for sampling purposes, taking out the cultured cells and the culture medium as samples out of the culture container 11.

The material of the tubes 12 may be selected appropriately in accordance with the application environment. Examples include: silicone rubber; soft vinyl chloride resins; polybutadiene resins; ethylene-vinyl acetate copolymers; chlorinated polyethylene resins; polyurethane thermoplastic elastomers; polyester thermoplastic elastomers; silicone thermoplastic elastomers; styrene elastomers such as SBS (styrene-butadiene-styrene), SIS (styrene-isoprene-styrene), SEBS (styrene-ethylene-butylene-styrene), and SEPS (styrene-ethylene-propylene-styrene); polyolefin resins; and fluorine resins.

The loading base 13 is a plane table with the culture container 11 placed on the top face. On the top face of the culture container 11, the agitating member 14 is mounted.

At each of four corners of the top face of the loading base 13 where the culture container 11 is placed, a stopper 13-1 is disposed upright. Meanwhile, at each of four corners of the culture container 11, a hole 11-2 is pierced through which the corresponding stopper 13-1 is inserted.

Inserting the stoppers 13-1 inserted through the holes 11-2 secures the culture container 11 on the top face of the loading base 13. This also prevents misalignment of the culture container 11 with the movement of the agitating member 14.

It should be noted that the stoppers will not be limited to the above members. It is possible to use any type of stoppers insofar as the stoppers have a prevention mechanism of misalignment of the culture container 11.

The agitating member 14 applies an external force onto the culture container 11 to control cell aggregate formation and cell aggregate disintegration with respect to cells disposed in the culture container 11.

In the method for culturing cells according to this embodiment, as shown in FIG. 3, the agitating member 14 presses the culture container 11 to a predetermined pressing degree and moves at a predetermined speed in parallel to the loading base 13. This movement is repeated with a predetermined cycle. Examples of the agitating member 14 used include a roller.

In this manner, the agitating member 14 in this embodiment employs application an external force onto a culture container to ensure fine adjustment of agitation effected in the culture container 11. This ensures appropriate agitation for cell aggregate formation and ensures appropriate agitation for cell aggregate disintegration.

As shown in FIG. 1, a supporting stand 15 includes: upright bearing portions disposed at respective positions of both sides of the loading base 13 to rotatably support both ends of the agitating member 14; and a connection member to couple the bearing portions to one another.

As shown in FIG. 2, the supporting stand 15 is movable upward and downward by a rod type electric cylinder 17 (actuator for actuation in the vertical direction) placed beneath the connection member. This ensures fine adjustment, on a 0.1 mm basis, of the pressing degree of the agitating member 14 secured to the supporting stand 15 against the culture container 11.

Further, the rod type electric cylinder 17 is secured to a moving carriage 16 on a slider type electric cylinder 21 (actuator for actuation in the horizontal direction) to permit movement in the horizontal direction relative to the loading base 13. In order to adjust the moving speed of the agitating member 14 secured to the supporting stand 15, the moving speed of the moving carriage 16 in the horizontal direction is controlled.

The supporting stand 15, the moving carriage 16, the rod type electric cylinder 17, and the slider type electric cylinder 21 constitute a driving device of the cell culturing apparatus 10 according to this embodiment.

Thus, with the cell culturing apparatus 10 according to this embodiment, the rod type electric cylinder 17 and the slider type electric cylinder 21 are used to adjust the pressing degree of the agitating member 14 against the culture container 11 and to adjust the moving speed of the agitating member 14. This ensures control of agitation of the culture solution in the culture container 11 to optimize the size of aggregates of the cells.

The operation control of the agitation member may be by other than the electric actuators such as the rod type electric cylinder 17 and the slider type electric cylinder 21. It is also possible to use actuators utilizing air pressure, oil pressure, or an electromagnetic force, or use motors and cams.

<Formation of Aggregate of Cell>

As shown in FIG. 4, in cell culturing, there is an appropriate size of an aggregate of cells depending on the kind of cells used for culturing.

That is, cultured cells have such a characteristic that an individual cell has a low division rate, and it is when cells adhere to form a certain amount of aggregate that adequate division starts. In the usual stationary culturing, when the cell density is low at an early stage of culturing, cells adhere by dispersion and gradually form aggregates, though at a comparatively low rate.

In view of this, conventional cell culturing uses, for example, a well plate at an early stage of culturing to forcibly gather cells at one place of high density, where the cells adhere easily. Alternatively, a container of small capacity is used first and then a large container is used as the cells proliferate. Thus, the cells are cultured while preventing lowering of the cell density.

In contrast, in this embodiment, agitation causes the cells floating on the bottom of the culture container 11 to move actively to increase the probability of cell adhesion, ensuring earlier formation of aggregates of appropriate size.

Consequently, according to the method for culturing cells employing the cell culturing apparatus 10 according to this embodiment, when the cells are separated from each other at the time of start of cell culturing, the formation of aggregates of appropriate size is promoted by bringing the cells into contact with each other. This improves cell proliferation efficiency.

Further, such cell aggregate formation control is not limited to an early stage of culturing (at the time of seeding). Other suitable examples include the case where the aggregates collapse and the cells are separated from each other as a result of application of an excess external force to the culture container 11 during cell culturing. This, as a result, improves cell proliferation efficiency.

<Disintegration of Aggregate of Cells>

Meanwhile, if an aggregate of cells is excessively large, a lack of oxygen and a lack of nutrients occur in the inner side of the aggregate, resulting in degraded cell proliferation efficiency.

In view of this, when an aggregate becomes large, it is preferable to cause a strong flow (turbulent flow) in the culture solution to disintegrate the aggregates.

According to the method for culturing cells employing the cell culturing apparatus 10 according to this embodiment, when an aggregate becomes large, the pressing degree and speed of the agitating member 14 is adjusted to control agitation to cause a strong flow in the culture solution, thereby disintegrating the aggregate into an appropriate size.

As described above, with the cell culturing apparatus 10 according to this embodiment and the method for culturing cells employing the cell culturing apparatus 10, the agitating member 14 presses the culture container 11 to a predetermined pressing degree and moves at a predetermined speed in parallel to the loading base 13. This ensures appropriate control of the strength of an external force applied onto the culture container 11.

Consequently, the fine adjustment of the agitation in the culture container 11 ensures appropriate agitation for cell aggregate formation, and also ensures appropriate agitation for cell aggregate disintegration while ensuring that the cells are not separated from each other. This ensures adjustment of the size of a cell aggregate to a size appropriate for proliferation.

[Second Embodiment]

Next, referring to FIG. 5, a second embodiment of the present invention will be described. The figure is a diagram illustrating the cell culturing apparatus according to this embodiment.

This embodiment is different from the first embodiment in that the cell culturing apparatus 10 has the culture container 11 divided into a culture portion and an expansion portion by a partition member so as to make the capacity of the culture medium adjustable to an appropriate size in accordance with the proliferation of cells, with the culture portion being agitatable by the agitating member 14 (agitating roller). Further, in this embodiment, both ends of the culture container 11 are secured by clamp members 23. This embodiment is otherwise similar to the first embodiment.

Figure 5:
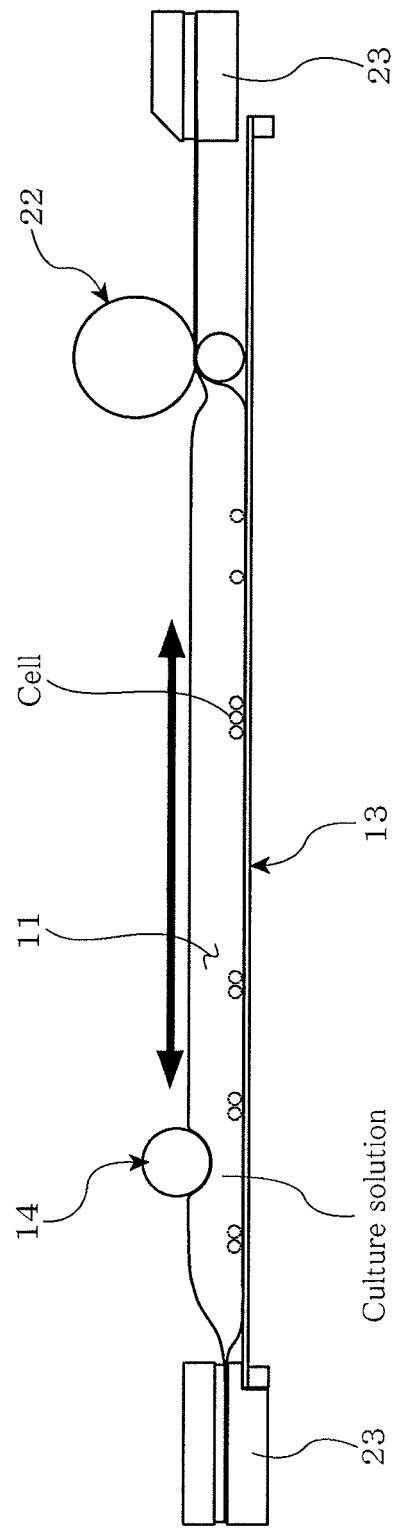
FIG. 5 is a diagram illustrating a cell culturing apparatus according to a second embodiment of the present invention.

That is, as shown in FIG. 5, in the cell culturing apparatus 10 according to this embodiment, the culture container 11 is divided by partition rollers (partition member) 22 to provide a culture portion in which a culture solution and cells are enclosed, and an expansion portion that expands the capacity of the culture portion with the movement of the partition rollers 22. The partition rollers 22 are disposed in parallel to the agitating member (agitating roller) 14, and movable in parallel to the loading base 13.

Use of the partition rollers 22 ensures a continuous change in the capacity of the culture portion. That is, the partition rollers 22 move with the proliferation of cells to increase the capacity of the culture portion, thus maintaining the cell density within an appropriate range.

While in the example shown in the above figure the partition is implemented by vertically pinching the culture container 11 between two partition rollers 22, this should not be construed in a limiting sense. For example, it is also possible to use a single partition roller 22 to press from upward the culture container 11 against the loading base 13, thus partitioning the culture container 11 into a culture portion and an expansion portion.

WO2008/136371 and WO2008/136339, both filed by the applicant, describe a technique to control the culture capacity using a partition member so as to improve culture efficiency.

According to the cell culturing apparatus 10 according to this embodiment and the method for culturing cells employing the cell culturing apparatus 10, use of the partition rollers 22 ensures control of the culture capacity at a level that ensures high cell proliferation efficiency. Use of the partition rollers 22 also ensures adjustment of the size of a cell aggregate in the culture portion to a size that ensures high cell proliferation efficiency.

This results in further improved cell proliferation efficiency.

[Third Embodiment]

Next, a third embodiment of the present invention will be described by referring to FIG. 6. This figure is a diagram illustrating the cell culturing apparatus 10 according to this embodiment.

This embodiment is different from the first embodiment in the following respects. The cells in the culture container 11 are photographed. Whether the size of an aggregate is within a predetermined range is determined automatically. The size of aggregates is adjusted to an appropriate size based on the determination. This embodiment is otherwise similar to the first embodiment.

Figure 6:
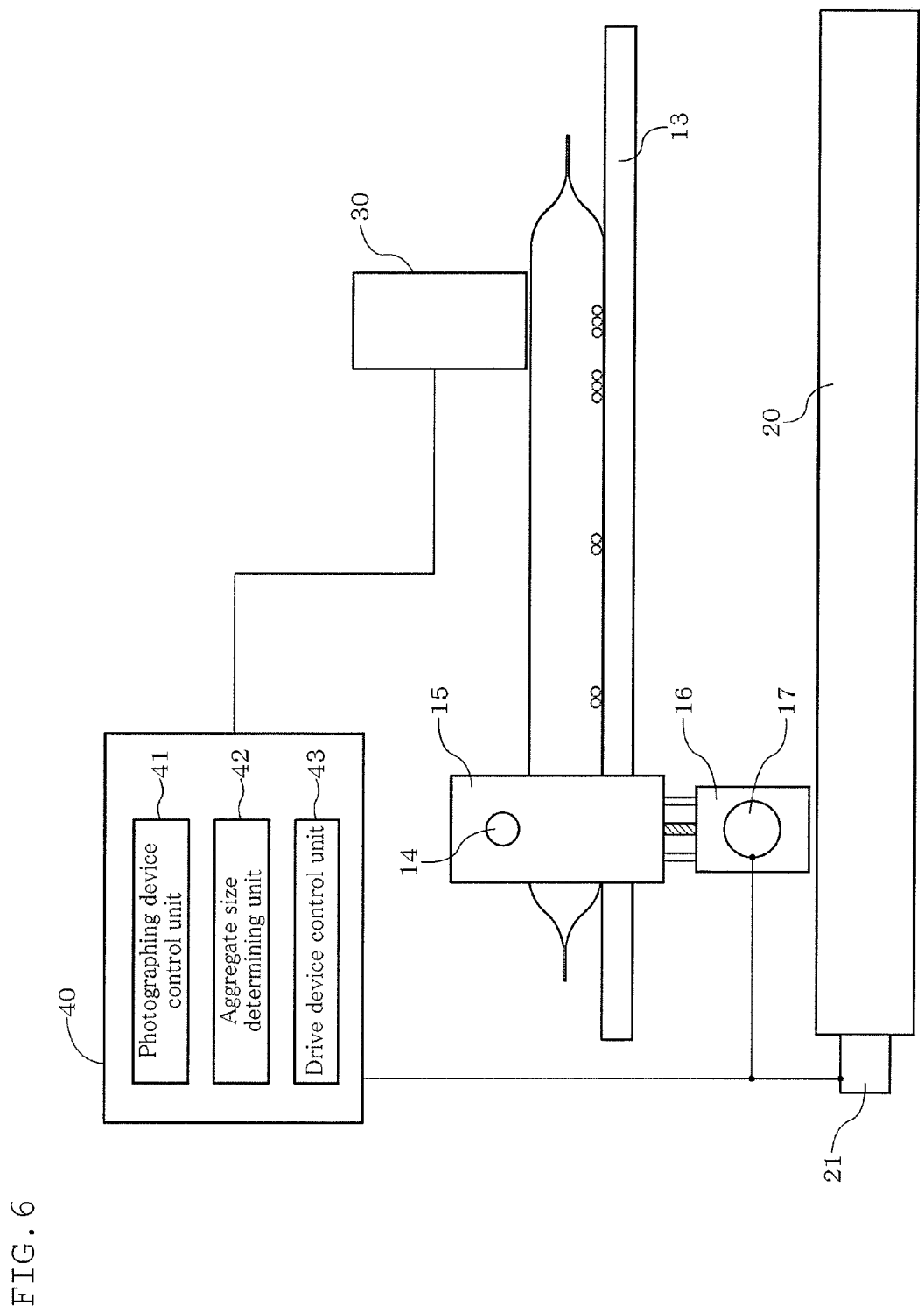
FIG. 6 is a diagram illustrating a cell culturing apparatus according to a third embodiment of the present invention.

Specifically, as shown in FIG. 6, the cell culturing apparatus 10 according to this embodiment includes a photographing device 30 and a control device 40, in addition to the configuration of the first embodiment.

Upon receipt of instruction information of photographing from the control device 40, the photographing device 30 photographs the cells in the culture container 11, and transmits the obtained image to the control device 40. The instruction information of photographing for the photographing device 30 may be transmitted automatically with a predetermined timing from the control device 40.

Examples of the photographing device 30 used include a CCD camera secured to a lens barrel of a phase contrast microscope.

The control device 40 is an information processing device that controls a driving device to move the agitating member 14 in the cell culturing apparatus 10 and controls the photographing device 30. As shown in FIG. 6, the control device 40 includes a photographing device control unit 41, an aggregate size determining unit 42, and a driving device control unit 43.

The photographing device control unit 41 transmits the instruction information to cause the photographing device 30 to carry out photographing with a predetermined timing, and receives the photographed image from the photographing device 30.

When the photographing device control unit 41 receives an image, the aggregate size determining unit 42 determines whether the size of the cell aggregate in this image information is within a predetermined range. Examples of the predetermined range include 100 μm to 600 μm. The size of the aggregate may be the average value of photographed aggregates.

As a result of the determination, when the size of the cell aggregate is below or above the predetermined range, the determination result is output to the driving device control unit 43.

The driving device control unit 43 determines the pressing degree, moving speed, and moving cycle of the agitating member 14 based on the determination result input from the aggregate size determining unit 42, and controls the rod type electric cylinder 17 and the slider type electric cylinder 21 based on these driving conditions.

Thus, when the size of the cell aggregate is below the predetermined range, the cell aggregate in the culture container 11 is increased to an appropriate size, while when the size of the cell aggregate is above the predetermined range, the cell aggregate is disintegrated into an appropriate size. This ensures adjustment of the size of the cell aggregate to an optimal size for proliferation.

In order to carry out this processing, the control device 40 or the driving device control unit 43 preferably has a table that memorizes various aggregate sizes in relation to data of appropriate pressing degree, moving speed, and moving cycle of the agitating member 14.

As described above, with the cell culturing apparatus 10 according to this embodiment and the method for culturing cells employing the cell culturing apparatus 10, the size of an aggregate in the culture container 11 is adjusted automatically. This improves cell proliferation efficiency stably.

Figure 7:
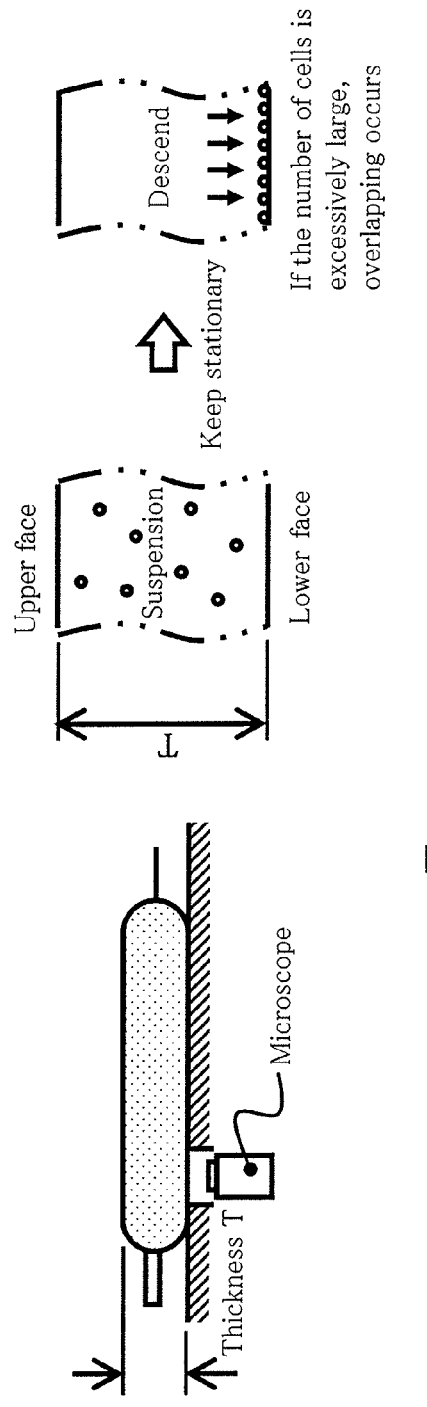
FIG. 7 is a diagram illustrating the principle of a counting method of the present invention for counted targets in a container.
Figure 7:
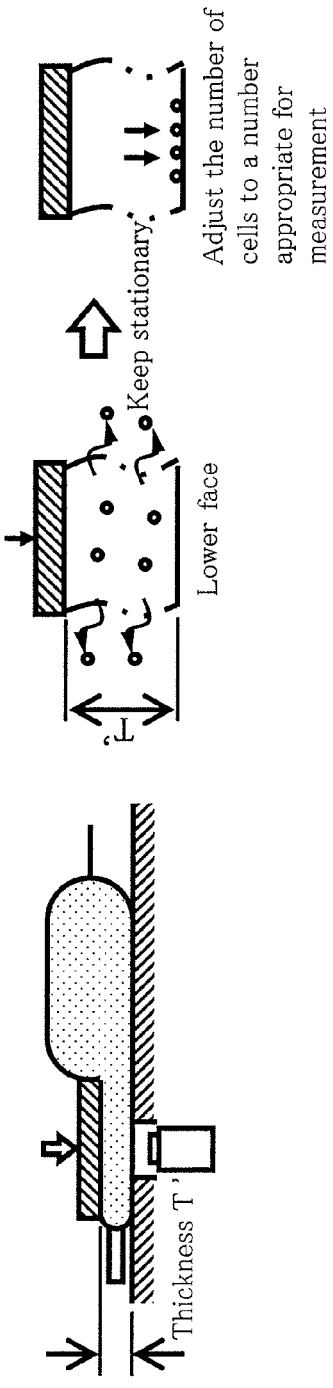

Next, referring to FIG. 7, description will be given with regard to a principle of the method for counting counted targets disposed in a container according to an embodiment of the present invention. The figure shows how the cells in the culture container are directly observed through a microscope and the number of the cells is counted. FIG. 7(A) shows conventional observation, which does not involve adjustment of the thickness of the container. Use of a culture solution having a specific gravity smaller than that of the cells causes the cells to sink to the bottom of the container, which is a suitable state for observation through a microscope. It is also possible to use a culture solution having a large specific gravity, in which case the cells are gathered at an upper portion of the container, where the cells are observed.

In the case of FIG. 7(A), as the number of cells in the container increases, the cells gradually overlap with each other when the cells are suspended and made stationary. Accordingly, this method does not provide accurate counting of the number of cells in large-scale cell culturing.

In view of this, in this embodiment of the present invention, when the number of the cells is excessively high for accurate correcting, the thickness of the container is reduced as shown in FIG. 7(B) to reduce the number of the cells in an observation region (measurement target region), thus adjusting the number of the cells to a number suitable for measurement.

Thus, even in the case of large-scale cell culturing using a culture container, the direct observation of cells in the culture container ensures counting of the number of cells without disassembling of the culture system.

Further, when the number of cells is excessively small in the culture container and thus it is difficult to prospect the density throughout the culture container, increasing the thickness of the container increases the number of the cells in the observation region, thus adjusting the number of the cells to a number suitable for measurement.

[Fourth Embodiment]

Next, referring to FIG. 8, description will be made with respect to a method for counting counted targets disposed in a container and a counting apparatus according to a fourth embodiment of the present invention. The figure is a diagram illustrating the counting apparatus according to this embodiment. As shown in the figure, a counting apparatus 50 according to this embodiment includes a thickness adjusting member 51, a loading base 13, photographing means 52, a driving device 53, a driving device 54, and an illumination source 55. With culture container 11 disposed on the loading base 13, the number of cultured cells in the culture container 11 is counted.

The thickness adjusting member 51 adjusts the thickness of the culture container 11 on the loading base 13. In the example shown in FIG. 8, the thickness adjusting member 51 includes a pressing plate having a flat portion used to press the culture container 11, and presses from upward a part of the culture container 11, which is made of a soft packing material, from the upper side to reduce the thickness of the culture container 11.

At least a part of the thickness adjusting member 51 located above the measurement target region of the culture container 11 is made of a transparent material. This ensures observation from downward by the photographing means 52, which includes a microscope and a CCD camera, with illumination from upward by the illumination source 55.

Figure 8:
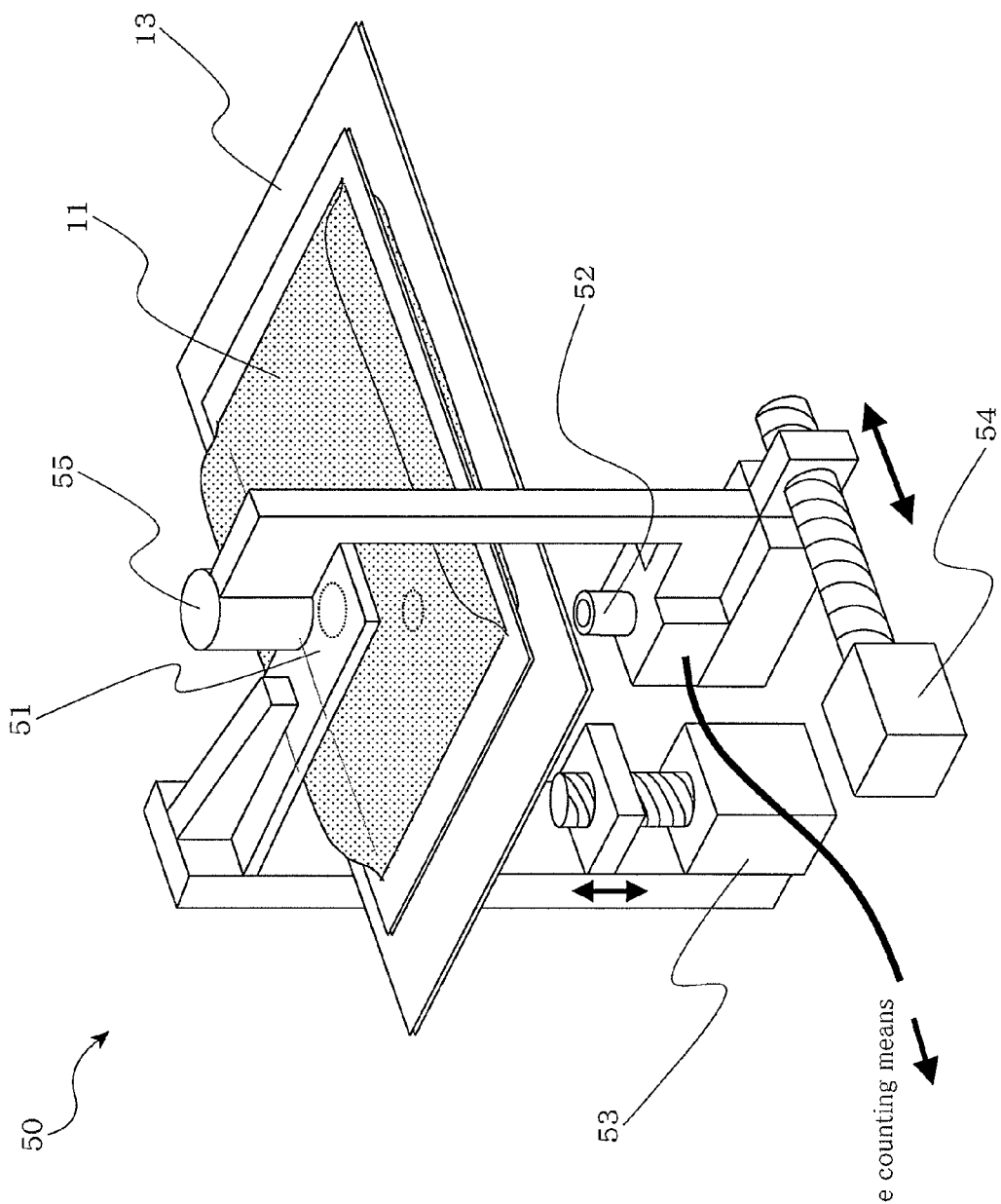
FIG. 8 is a diagram illustrating a counting apparatus according to a fourth embodiment of the present invention.

The thickness adjusting member 51 is not limited to the pressing plate to press the culture container 11 with the flat portion as shown in FIG. 8. For example, the thickness adjusting member 51 may include rollers or a stretching member.

For example, rollers may move while vertically nipping the culture container 11 from both sides or one side to reduce the horizontal area of the culture container 11, thus increasing the thickness of the culture container 11. In contrast, increasing the horizontal area of the culture container 11 reduces the thickness of the culture container 11. When a stretching member is used to stretch the culture container 11 in the horizontal direction, the thickness of the culture container 11 is also reduced.

The loading base 13 is a flat base on which the culture container 11 is placed, and constitutes a placing device for counting, together with the thickness adjust member 51.

A part of the loading base 13 positioned beneath the measurement target region is made of a transparent member such as a glass plate 56 to permit observation of the culture container 11 from downward by the photographing means 52.

The driving device 53 moves the thickness adjusting member 51 upward and downward via ball screws as shown in FIG. 8. This permits the thickness adjusting member 51 to press the culture container 11 on the loading base 13 and to adjust the thickness of the culture container 11.

Examples of the driving device 53 include a rod type electric cylinder (actuator for actuation in the vertical direction). This ensures that the thickness of the culture container 11 is finely adjusted, on a 0.01 mm basis.

The driving device 54 moves the photographing means 52 in the horizontal direction relative to the loading base 13 by ball screws as shown in FIG. 8. The driving device 54 keeps the photographing means 52 arranged outside the loading base 13 except during photographing of cells in the culture container 11, and at the time of photographing, moves the photographing means 52 to a position beneath the measurement target region of the culture container 11.

The driving device 53 and the driving device 54 may be other than electric actuators. It is also possible to use actuators utilizing air pressure, oil pressure, or an electromagnetic force, or use motors and cams.

The illumination source 55 illuminates the measurement target region in the culture container 11 through the thickness adjusting member 51, and provides brightness required for photographing of cells by the photographing means 52. In this respect, the amount of transmitted light varies depending on the adjusted thickness of the culture solution, which may cause difference in contrast among photographed images. In view of this, it is preferable to adjust the amount of light in accordance with the thickness of the culture solution.

The culture container 11 may be similar to that in the first embodiment.

Figure 9:
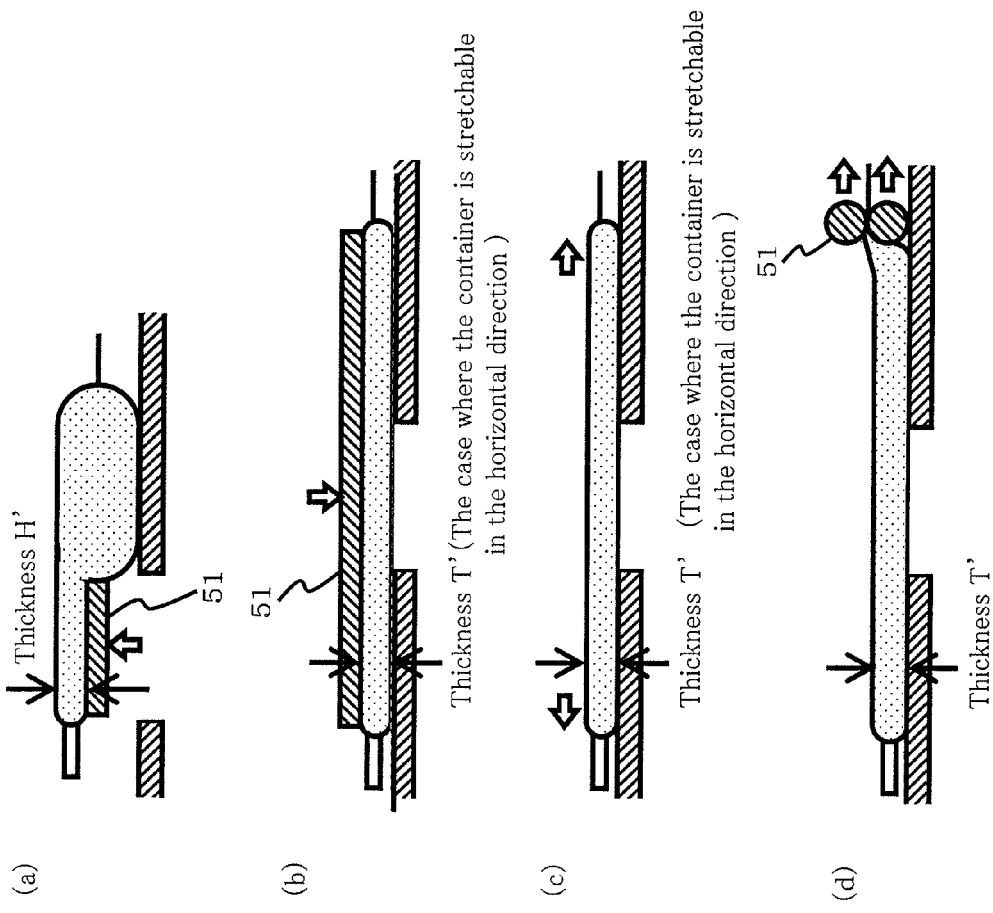
FIG. 9 is a diagram illustrating a method of adjusting the thickness of a container (the case of reducing the thickness) using the counting apparatus according to the fourth embodiment of the present invention.
Figure 10:
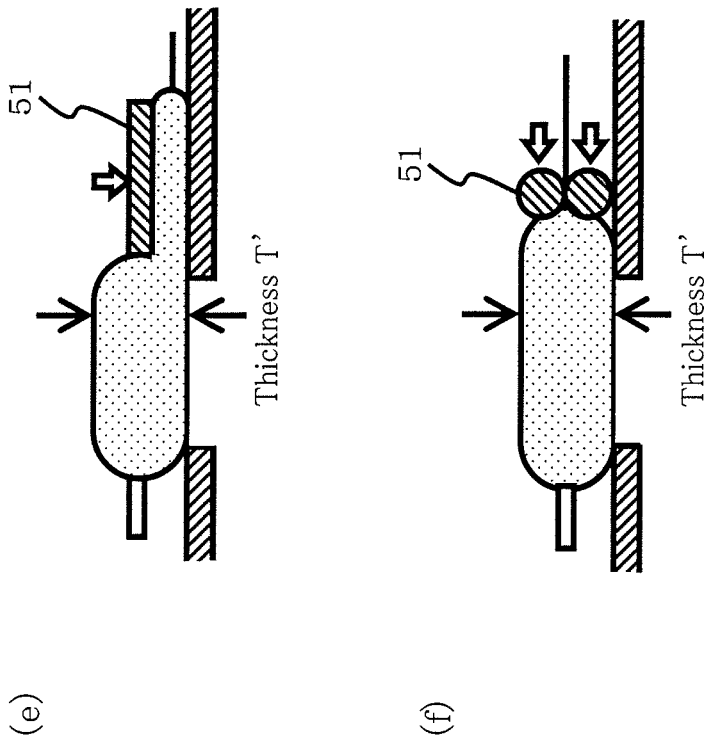
FIG. 10 is a diagram illustrating a method of adjusting the thickness of a container (the case of increasing the thickness) using the counting apparatus according to the fourth embodiment of the present invention.

Next, referring to FIG. 9 and FIG. 10, description will be made with respect to an example of the adjustment of the thickness of the culture container 11 by the counting apparatus according to this embodiment. FIG. 9 shows a case where the thickness of the container is reduced, and FIG. 10 shows a case where the thickness of the container is increased.

When the thickness of the culture container 11 is reduced, the adjustment of the thickness of the container may be other than the example shown in FIG. 8. For example, as shown in (a) of FIG. 9, the thickness adjusting member 51 may press the culture container 11 from downward. In this respect, it is preferable to fix the position of the upper face of the culture container 11 with a glass plate or the like, an illustration of which is omitted.

When the culture container 11 is made of a horizontally stretchable material, the thickness of the culture container 11 may be reduced by pressing the culture container 11 using a thickness adjusting member 51 capable of covering the entire surface of the culture container 11 as shown in (b) of FIG. 9. As shown in (c) of FIG. 9, it is also possible to reduce the thickness of the culture container 11 by stretching the culture container 11 using a thickness adjusting member 51. In this case, the culture container 11 may be stretched with one edge of the culture container 11 fixed and the other edge opposite in the horizon direction stretched using a thickness adjusting member 51 that includes a stretching member. Alternatively, both ends of the culture container 11 may be stretched in the horizon direction using two thickness adjusting members 51. Examples of the material of the flexible culture container 11 include silicone rubbers.

As shown in (d) of FIG. 9, it is also possible to use rollers and the like as thickness adjusting members 51, in which case the rollers move to increase the horizontal area of the culture container 11, thus reducing the thickness of the culture container 11.

When the thickness of the container is increased, for example, as shown in (e) of FIG. 10, the thickness adjusting member 51 may press a part of the top face of the culture container 11. This increases the thickness of a part of the culture container 11 other than the pressed part.

As shown in (f) of FIG. 10, it is also possible to use rollers and the like as thickness adjusting members 51, in which case the rollers move to reduce the horizontal area of the culture container 11, thus increasing the thickness of the culture container 11.

Next, a method for counting counted targets in the container according to this embodiment will be described in detail by referring to FIG. 8.

First, it is preferable to agitate the culture solution disposed in the culture container 11 prior to the step of counting the number of the cells disposed in the culture container 11. It is noted that the agitating means for a culture solution will be described in detail in the fifth embodiment.

Next, the driving device 54 moves the photographing means 52 to beneath the measurement target region of the culture container 11.

Next, the driving device 53 moves the thickness adjusting member 51 downward by to adjust the thickness of the culture container 11 to a predetermined thickness.

In this respect, the predetermined thickness may be determined on various values depending on the kind of the cells, the size of the culture container, the area of the measurement target region, and the period for culturing.

Next, the measurement target region is illuminated by the illumination source 55, and photographed by the photographing means 52. Then, the number of cells in the photographed image is counted. In this respect, the photographed image is transmitted from the photographing means 52 to counting means and the number of the cells are automatically counted by the counting means. The counting means may be a known cell counting analyzing device and cell counting apparatus.

In this embodiment, the culture solution has a specific gravity smaller than that of cultured cells, and hence the cultured cells are precipitated on the bottom of the culture container 11. The photographing means focuses on the precipitated cells to photograph the cells. When, however, the cells have a large density and overlap with each other in the measurement target region, the number of cells may not be counted accurately.

In view of this, in the method for counting counted targets disposed in a container according to this embodiment, when cells overlap with each other in the measurement target region as described above, the thickness adjusting member 51 moves to reduce the thickness of the culture container 11 and thus to reduce the number of cells in the measurement target region. This ensures a countable number of cells.

The maximum number of cells that can be observed without cell overlapping in the measurement target region may be assumed approximately at less than a number obtained by dividing the area of the measurement target region by the average horizontal area of the cultured cells. In view of this, when as a result of counting of the number of cells, the counted number of cells is equal to or more than the maximum number of cells, it is preferable to reduce the thickness of the culture container 11 and then carry out the counting again. It is further possible to use other values in determining whether to adjust the thickness of the culture container 11, examples of the values include an accurately predicted number of densely arranged cells in the measurement target region. The predicted number may be used as the maximum number of cells.

Furthermore, when as a result of counting of the number of cells, the counted number of the cells is less than a predetermined value, the accuracy of the resultant cell density is low. In view of this, it is preferable to increase the thickness of the culture container 11 and then carry out the counting again. The sixth embodiment describes in detail a counting apparatus used for the above-described increasing of the thickness of the culture container 11.

The number of the cells in the measurement target region is counted in this manner, and then the number of cells is divided by the volume of the measurement target region, thus calculating the cell density. Further, the obtained cell density is multiplied by the volume of the culture container 11, thus calculating the number of cells disposed throughout the culture container 11.

The counting means is able to automatically calculate the cell density and the number of cells disposed throughout the culture container 11.

Thus, according to this embodiment, even when the number of cells in the culture container 11 is excessively large for accurate counting of the number of cells by direct observation of the culture container 11, reducing the thickness of the culture container 11 ensures counting of the number of cells. This ensures calculation of the density of the cells in the culture container 11.

[Fifth Embodiment]

Figure 11:
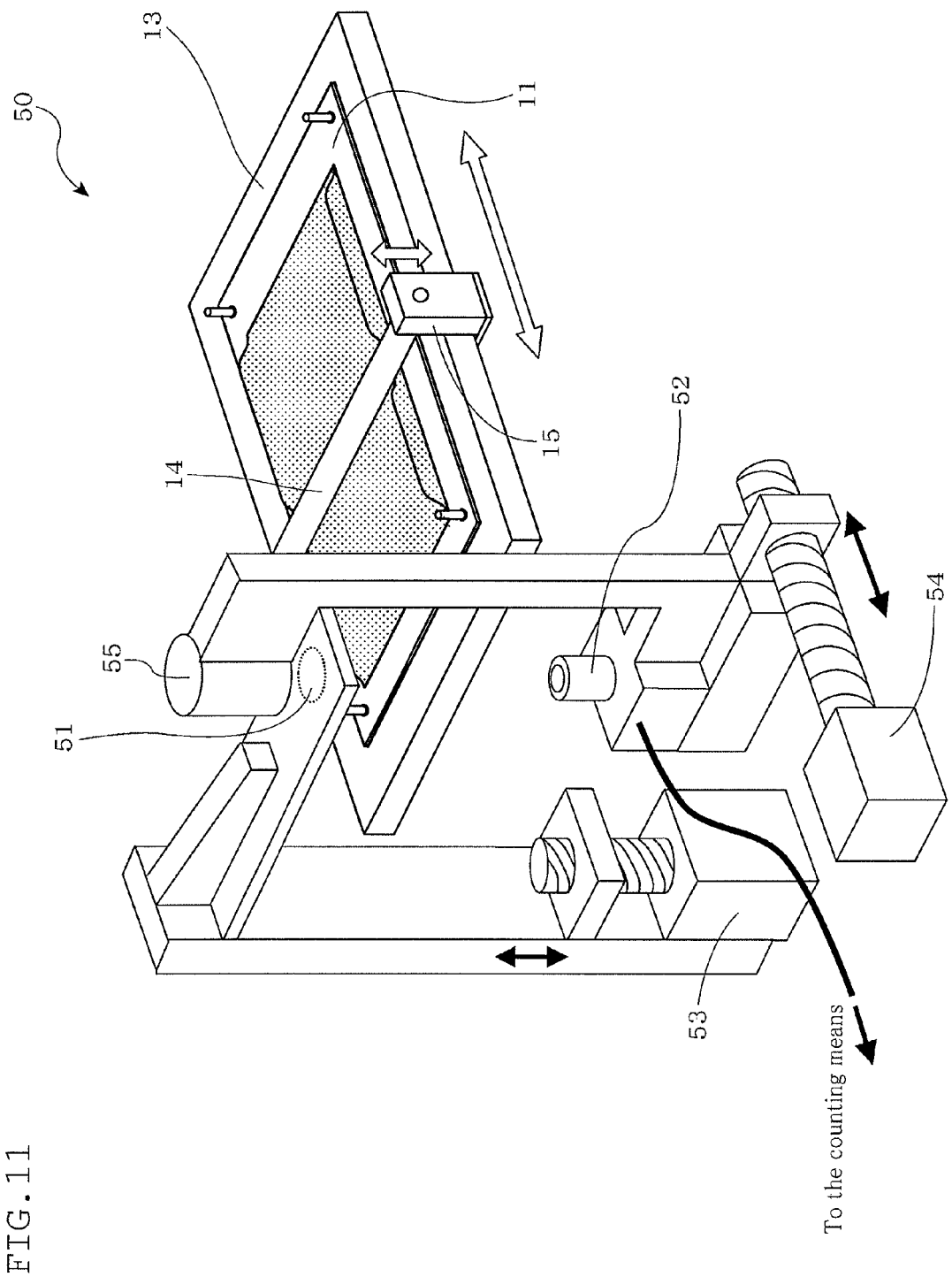
FIG. 11 is a diagram illustrating a counting apparatus according to a fifth embodiment of the present invention.

Next, referring to FIG. 11 and FIG. 2, description will given with regard to a counting method and a counting apparatus to count counted targets disposed in a container according to the fifth embodiment of the present invention. FIG. 11 is a diagram illustrating the counting apparatus according to this embodiment. FIG. 2 is a diagram illustrating a driving device (for an agitating member) of the cell culturing apparatus according to the first embodiment. In this embodiment, a similar apparatus may be used.

The counting apparatus according to this embodiment includes an agitating member in addition to the configuration of the counting apparatus according to the fourth embodiment. In this embodiment, agitating the culture solution disposed in the culture container 11 using the agitating member disperses the culture solution to make the cells easily observable. This embodiment may be otherwise similar to the fourth embodiment.

The agitating member 14 moves while pressing the culture container 11 to agitate the culture solution in the culture container 11 and disperse the cultured cells in the culture solution. Examples of the agitating member 14 include a roller as shown in FIG. 11.

In the example shown in this figure, the agitating member 14 presses the culture container 11 to a predetermined pressing degree, and at the same time, the agitating member 14 moves at a predetermined speed in parallel to the loading base 13 repeatedly with a predetermined cycle, thus agitating the culture solution.

As shown in FIG. 11, a supporting stand 15 includes: upright bearing portions disposed at respective positions of both sides of the loading base 13 to rotatably support both ends of the agitating member 14; and a connection member to couple the bearing portions to one another.

As shown in FIG. 2, the supporting stand 15 is movable upward and downward by a rod type electric cylinder 17 (actuator for actuation in the vertical direction) placed beneath the connection member. This ensures fine adjustment, on a 0.1 mm basis, of the pressing degree of the agitating member 14 secured to the supporting stand 15 against the culture container 11.

Further, the rod type electric cylinder 17 is secured to a moving carriage 16 on a slider type electric cylinder 21 (actuator for actuation in the horizontal direction) to permit movement in the horizontal direction relative to the loading base 13. In order to adjust the moving speed of the agitating member 14 secured to the supporting stand 15, the moving speed of the moving carriage 16 in the horizontal direction is controlled.

The operation control of the agitation member 14 may be by other than the electric actuators such as the rod type electric cylinder 17 and the slider type electric cylinder 21. It is also possible to use actuators utilizing air pressure, oil pressure, or an electromagnetic force, or use motors and cams.

With the counting method and counting apparatus to count counted targets disposed in a container according to this embodiment, prior to counting the number of cells in the culture container 11, the agitating member 14 makes reciprocating movement in the horizontal direction for a predetermined period of time with the agitating member 14 pressing the culture container 11 to a predetermined pressing degree.

This ensures that the culture solution in the culture container 11 is agitated to disperse the cultured cells disposed in the culture container 11 in a manner that facilitates counting of the number of the cultured cells.

[Sixth Embodiment]

Figure 12:
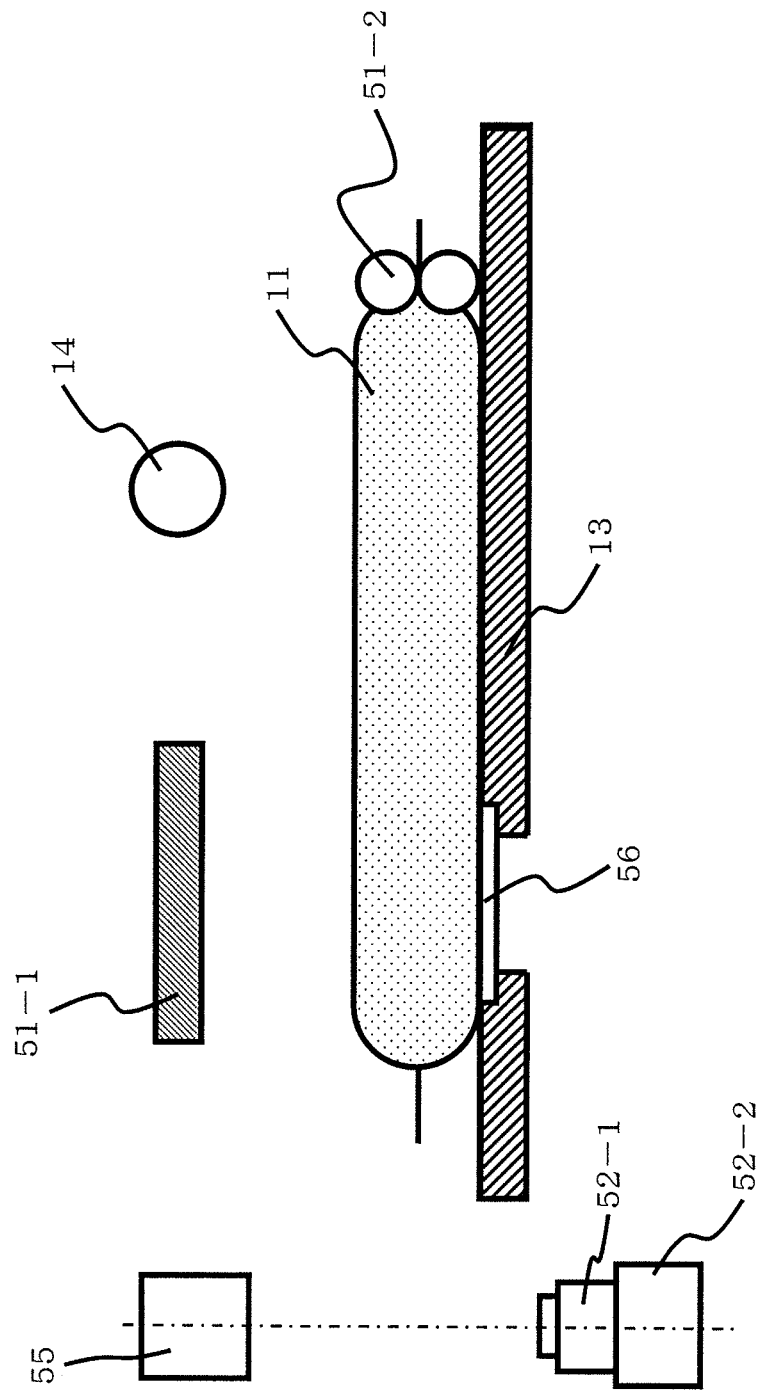
FIG. 12 is a diagram illustrating basic positions associated with a counting apparatus according to a sixth embodiment of the present invention.
Figure 13:
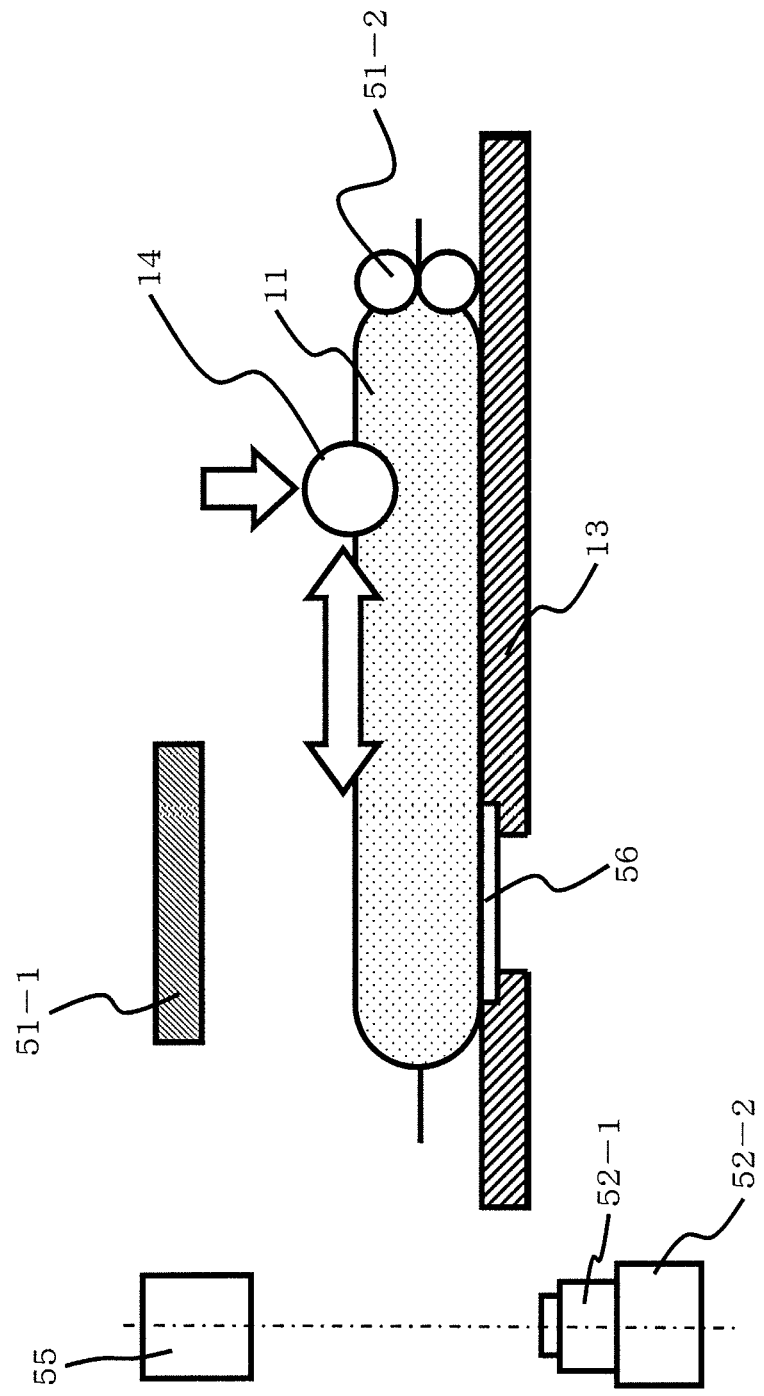
FIG. 13 is a diagram illustrating a state of agitation by the counting apparatus according to the sixth embodiment of the present invention.
Figure 14:
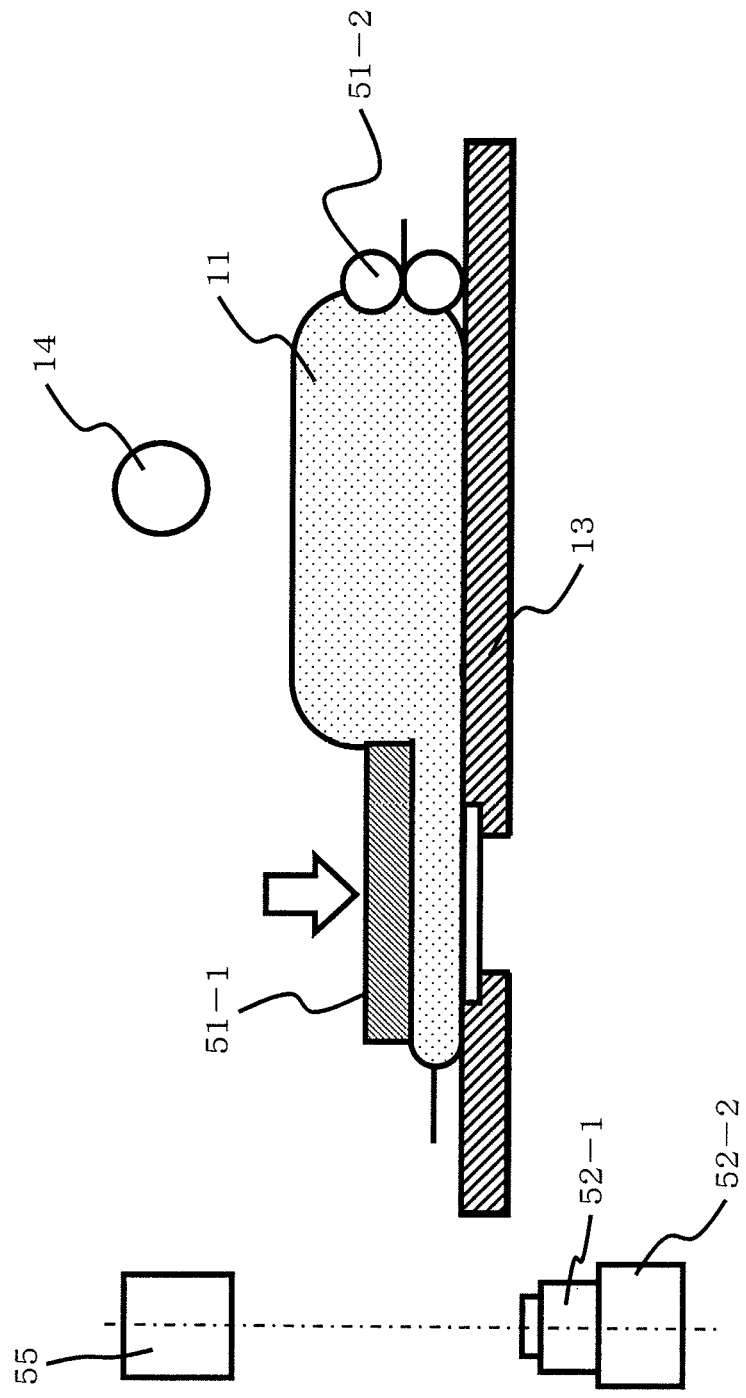
FIG. 14 is a diagram illustrating a state of thickness regulation and precipitation waiting (the case of reducing the thickness) on the counting apparatus according to the sixth embodiment of the present invention.
Figure 15:
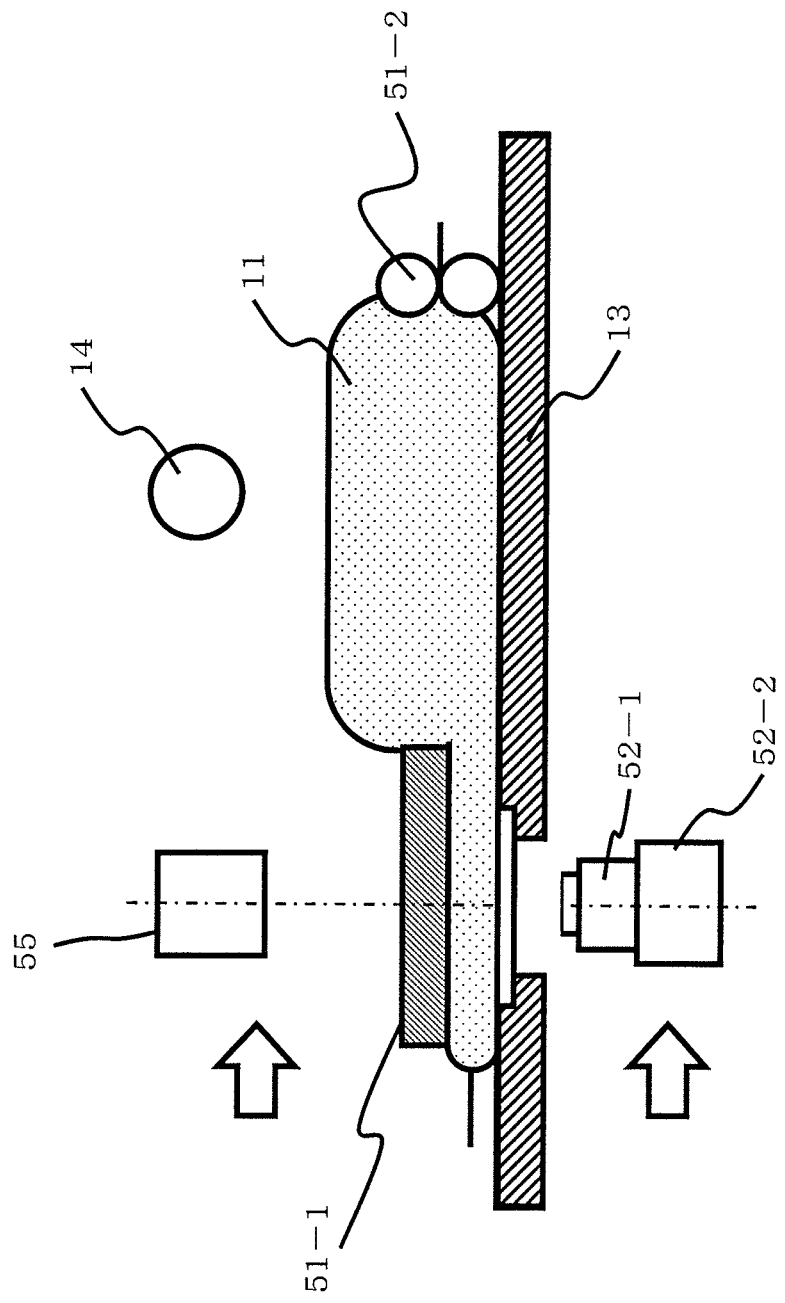
FIG. 15 is a diagram illustrating a state of microscope observation on the counting apparatus according to the sixth embodiment of the present invention.
Figure 16:
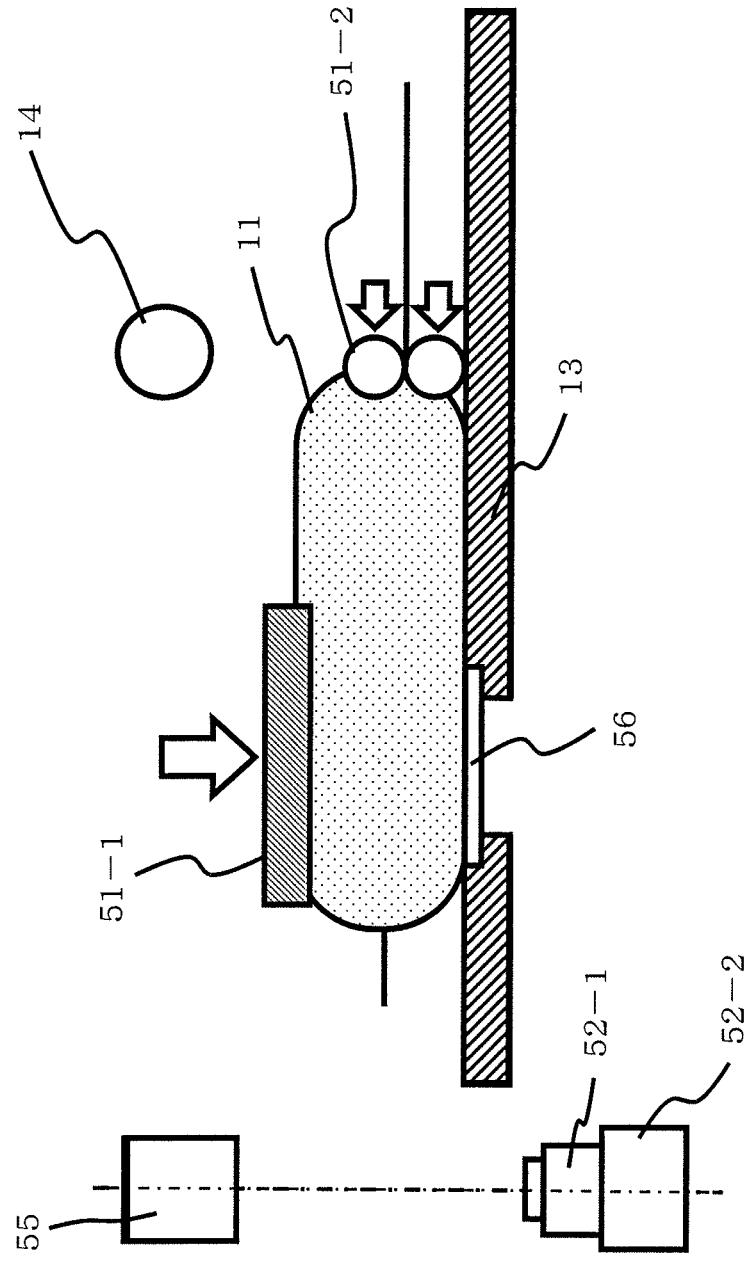
FIG. 16 is a diagram illustrating a state of thickness regulation and precipitation waiting (the case of increasing the thickness) on the counting apparatus according to the sixth embodiment of the present invention.

Next, referring to FIG. 12 through FIG. 16, description will given with regard to a counting method and a counting apparatus to count counted targets disposed in a container according to the sixth embodiment of the present invention. These figures are schematic diagrams showing a basic position (FIG. 12) of the counting apparatus in the method for counting counted targets disposed in a container according to this embodiment, a state of agitation (FIG. 13), a state of thickness regulation and precipitation waiting (when the number of cells to be counted is desired to be reduced: FIG. 14), a state of microscope observation (FIG. 15), and a state of thickness regulation and precipitation waiting (when the number of cells to be counted is desired to be increased: FIG. 16).

The counting apparatus according to this embodiment includes a thickness adjusting member to increase the thickness of the culture container 11 in addition to the configuration of the counting apparatus according to the fifth embodiment. This embodiment may be otherwise similar to the fifth embodiment.

Description will be given with regard to the operation procedure of the counting apparatus in the method for counting counted targets disposed in a container according to this embodiment of the present invention, along with the operations of increasing and reducing the thickness of the culture container 11.

(1) Basic Positions

First, referring to FIG. 12, the basic positions of the structural elements of the counting apparatus according to this embodiment will be described.

In this figure, the loading base 13 includes an observation hole for observation via a microscope, and a glass plate 56 constituting a part of the top face of the loading base 13 is fit in the upper part of the observation hole.

The culture container 11 is disposed on the loading base 13, and a thickness adjusting member 51-1 (pressing plate) is disposed above the observation hole of the loading base 13. The thickness adjusting member 51-1 moves downward to press the culture container 11, thus reducing the thickness of the culture container 11.

A thickness adjusting member 51-2 (roller) is disposed at one edge of the culture container 11. The thickness adjusting member 51-2 moves to reduce the horizontal area of the culture container 11, thus increasing the thickness of the culture container 11.

The agitating member 14 (roller) is disposed above the culture container 11. The agitating member 14 moves downward, and then the agitating member 14 moves in the horizontal direction while pressing the culture container 11 to agitate the culture solution disposed in the culture container 11.

Regarding the basic positions, a microscope 52-1 and a CCD camera 52-2 that constitute the photographing means 52 for photographing cells, and the illumination source 55 are arranged outside the loading base 13.

(2) Agitating State

Next, referring to FIG. 13, description will be made with respect to the procedure for agitating the culture solution in the culture container 11 prior to counting the number of counted targets in a container.

First, the agitating member 14 moves downward from its basic position shown in FIG. 12, and presses the culture container 11 to a predetermined pressing degree. Next, the agitating member 14 repeats a predetermined cycle of movement in parallel to the loading base 13 at a predetermined speed.

This ensures agitation of the culture solution disposed in the culture container 11 and equalization of the cells in the culture solution.

(3) Thickness-Regulating and Precipitation-Waiting State (Thickness Reduction)

Next, referring to FIG. 14, description will be made with respect to the procedure for reducing the thickness of the culture container 11 so as to reduce the number of cells to be counted.

First, the agitating member 14 moves upward to return to its basic position shown in FIG. 12, and then, the thickness adjusting member 51-1 moves downward to reduce the thickness of the culture container. In this respect, the thickness adjusting member 51-1 presses a part of the culture container 11 including a region above the observation hole of the loading base 13, thus adjusting the thickness of the measurement target region of the culture container 11 to a predetermined size. In this respect, under the culturing environment, as the thickness of the culture container 11 reduces, the number of cells to be counted reduces.

After the thickness of the culture container 11 is reduced, the culture container 11 is kept stationary until the cells in the culture container 11 precipitate.

(4) Microscope Observation State

Next, referring to FIG. 15, description will be made with respect to the procedure for counting the number of cells.

After the cells in the culture container 11 precipitate with the thickness of the culture container 11 reduced, as shown in FIG. 15, the photographing means, which includes the microscope 52-1 and the CCD camera 52-2, and the illumination source 55 move in the horizontal direction from their respective basic positions shown in FIG. 12 so that the photographing means 52 is disposed immediately beneath the observation hole and the illumination source 55 is disposed above the observation hole. Then, the cells that precipitate in the culture container 11 are photographed with the CCD camera 52-2.

The image captured in this manner is input to a counting apparatus, not shown, and the number of the cells in the image is counted by the counting apparatus. The density of the cells in the culture container 11 is calculated by dividing the obtained number of the cells by the volume of the measurement target region (the region of the culture container 11 observed by the CCD camera 52-2).

Thus, adjusting the thickness of the culture container 11 ensures accurate cell counting in the case where the cells in the culture container 11 proliferate enough to make their accurate counting difficult due to overlapping if the cells precipitate with the thickness of the culture container 11 remaining unchanged. This ensures calculation of the density of cells in the culture container 11 without disassembly of the culture system.

(5) Thickness-Regulating and Precipitation-Waiting State (Thickness Increment)

In an early stage of culturing, for example, the number of the cells is small. Although counting may be possible, the accuracy of the obtained density of the cells can turn out to be low.

In view of this, when the number of the cells is small, the thickness of the culture container 11 is increased as shown in FIG. 16 so as to increase the number of the cells in the measurement target region, prior to the microscope observation described in (4).

Specifically, after the agitation in (2), the agitating member 14 moves upward to return to its basic position shown in FIG. 12. Then, the thickness adjusting member 51-2 including a roller moves in the direction of the measurement target region to press the culture container 11, thus increasing the thickness of the culture container 11. In this respect, in order to make the thickness of the culture container 11 uniform in the measurement target region, the thickness adjusting member 51-1 moves to a position of contact with the top face of the culture container 11 on the measurement target region. Then, the culture container 11 is kept stationary until the cells in the culture container 11 precipitate.

This increases the number of the cells in the measurement target region, and ensures more accurate calculation of the density of the cells when the number of the cells in the culture container 11 is small.

A specific cell number for the smallness of the number of the cells in the culture container 11 may be determined based on the kind of the cells and the area of the measurement target region. Exemplary numbers include 0 and less than 10.

After the thickness of the culture container 11 is adjusted in accordance with the procedure of (1) through (5) described above, the thickness of the culture container 11 is adjusted again in accordance with the procedure of (1) through (5) and the number of cells is counted if any of the following occurs: overlapping is observed among the cells; no cell is observed; and approximately no cell is observed in the measurement target region.

Thus, with this embodiment, increasing the thickness of the culture container 11 ensures accurate calculation of the density of the cells in the culture container 11 when the number of the cells is small and an accurate cell density may not be obtained by observing the culture container 11 with the culture container 11 remaining unchanged.

EXAMPLE

Figures 17, 18:
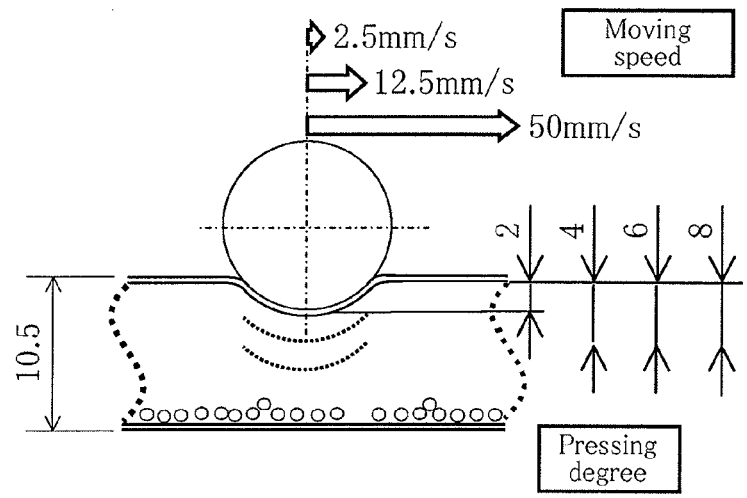
FIG. 17 is a diagram illustrating kinds of conditions of agitation by the cell culturing apparatus according to the first embodiment of the present invention.
FIG. 18 is a diagram showing cell states as a result of agitation by the cell culturing apparatus according to the first embodiment of the present invention under the respective agitation conditions.

Next, description will be made with respect to examples in which cells were cultured by the cell culturing apparatus 10 according to the first embodiment. First, referring to FIG. 17 and FIG. 18, various types of culture conditions and the degree of agitation in the respective types are described. FIG. 17 is a diagram illustrating kinds of conditions of agitation by the cell culturing apparatus 10 according to this embodiment, and FIG. 18 is a diagram showing cell states as a result of agitation under the agitation conditions.

As shown in FIG. 17, with the culturing method according to the embodiment of the present invention, the agitating member 14 presses the culture container 11 from upward, and then the agitating member 14 moves in parallel to the loading base 13, thus agitating the culture medium in the culture container 11.

The pressing degree of the agitating member 14 pressing the culture container 11 may be set at various values. For example, as shown in the figure, when the thickness of the culture container 11 is 10.5 mm, the pressing degree may be set at 2 mm, 4 mm, 6 mm, and 8 mm.

Further, the moving speed of the agitating member 14 is adjusted in accordance with the respective pressing degrees. This is for the purpose of controlling the agitation of the culture solution disposed in the culture container 11 in order to obtain appropriate agitation for cell aggregate formation and appropriate agitation for cell aggregate disintegration.

Examples of the moving speed of the agitating member 14 include 2.5 mm/s, 12.5 mm/s, and 50 mm/s, as shown in the figure.

While there is no specific limitation to the diameter of the agitating member 14, the diameter is preferably 0.5 time to 3.0 times the thickness of the culture container 11 for appropriate control of the agitation.

FIG. 18 shows how much the culture solution in the culture container 11 was agitated under the above-described agitation conditions.

As shown in the figure, all the cells in the culture container 11 kept descended at a pressing degree of 2 mm and at a moving speed of 2.5 mm/s or 12.5 mm/s; and at a pressing degree of 4 mm and at a moving speed of 2.5 mm/s.

In the present specification, such agitation is referred to as "weak agitation". Agitation in accordance with "weak agitation" promotes cell aggregate formation.

Meanwhile, the culture solution in the culture container 11 was agitated to some extent, but most of the cells kept descended at a pressing degree of 2 mm and at a moving speed of 50 mm/s, at a pressing degree of 4 mm and at a moving speed of 12.5 mm/s or 50 mm/s; at a pressing degree of 6 mm and at a moving speed of 2.5 mm/s or 12.5 mm/s; and at a pressing degree of 8 mm and at a moving speed of 2.5 mm/s, as shown in FIG. 18.

Further, the culture solution in the culture container 11 was agitated to some extent, and most of the cells kept afloat at a pressing degree of 6 mm and at a moving speed of 50 mm/s; and at a pressing degree of 8 mm and at a moving speed of 12.5 mm/s.

In the present specification, the agitating condition in the vicinity of the boundary between the state in which most of the cells keep descended and the state in which most of the cells keep afloat is referred to as "medium agitation". Agitation in accordance with "medium agitation" ensures adjustment of a cell aggregate to an appropriate size without excessive disintegration of the cell aggregate.

Meanwhile, the culture solution in the culture container 11 was agitated intensely and all the cells kept afloat at a pressing degree of 8 mm and at a moving speed of 50 mm/s in FIG. 18. In the present specification, the agitation that makes all the cells afloat is referred to as "strong agitation". Such "strong agitation" disintegrates a cell aggregate into individual cells. Repeating the "strong agitation" turns the cells into suspension state. However, if cells are separated from each other, proliferation efficiency degrades.

In the agitation in the conventional cell culturing, a culture container is agitated intensely, which corresponds to "strong agitation". This is problematic in that the agitation causes degradation of proliferation efficiency. The embodiments of the present invention solve this problem.

Next, description will be made with respect to examples in which the thickness of the culture container 11 was adjusted and then the number of cells was counted by the counting method and counting apparatus to count counted targets in a container according to the embodiment of the present invention. Description will be also made with respect to a comparative example in which the number of cells was counted without adjusting the thickness of the culture container 11.

Example 1

Figure 19:
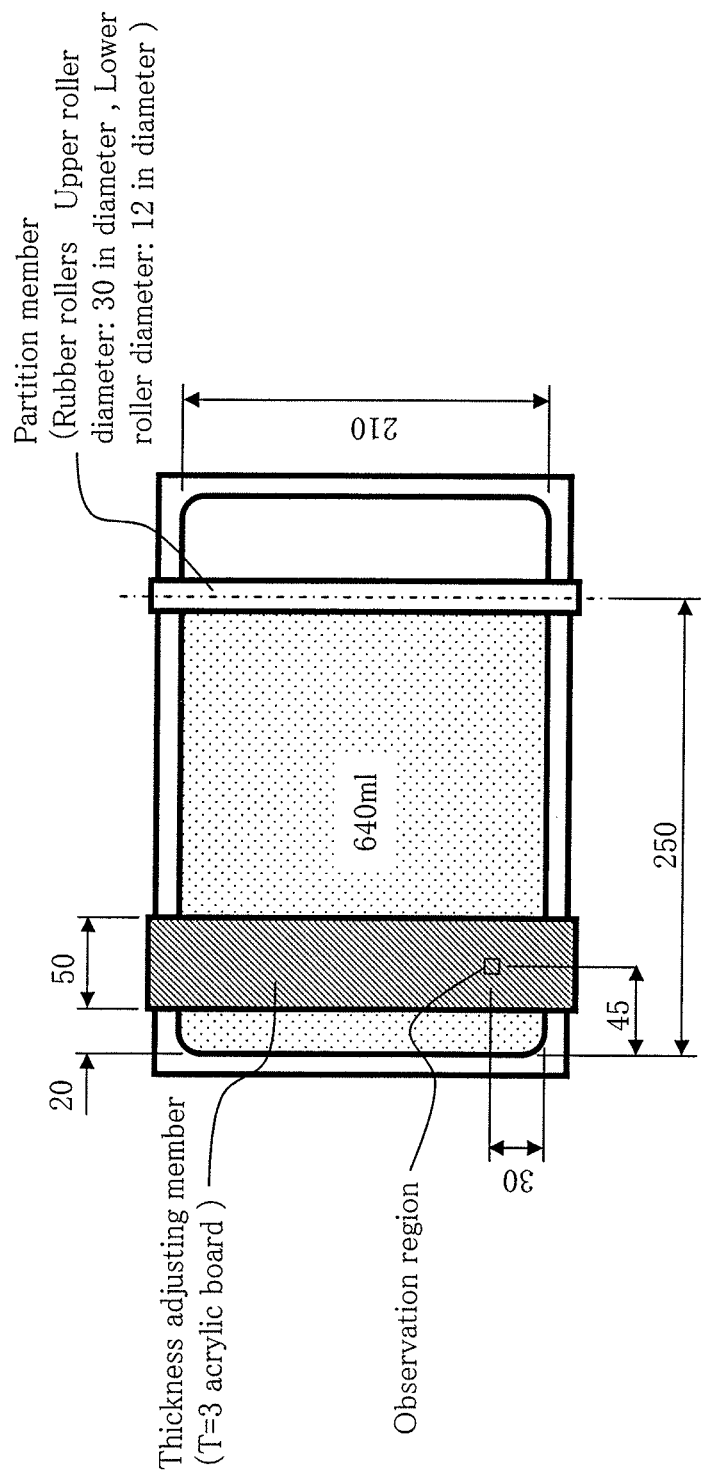
FIG. 19 is a diagram illustrating a culture container used in examples 1 to 5 of the present invention and comparative example 1.

As the culture container 11, a bag made of LDPE (linear low-density polyethylene) with a film thickness of 0.15 mm was used. As shown in FIG. 19, the culture container 11 was partitioned with a partition member (rubber roller) to form a culture portion serving as a culturing region with a longer side of 250 mm and a shorter side of 210 mm. A culture solution of 640 ml was put into the culture portion. In this respect, the thickness of the culture container 11 placed in flat orientation was approximately 16 mm, though the top face of the culture container 11 was not a perfectly horizontal surface. The horizontal surface of the observation region (measurement target region) was, in terms of size, a 0.5 mm by 0.5 mm square.

As the culture solution, AlyS5050N-0 culture medium available from Cell Science & Technology Institute, Inc. was used. The cultured cells used were JurkatE6.1 strains of human leukemia T lymphoma proliferated to a required amount in a cell culturing dish.

As the agitating member 14, a roller of 12 mm in diameter was used. Agitation was carried out under the agitation conditions of a pressing degree of 13 mm, a speed of 50 mm/s, and 10 times of reciprocation.

Figure 20:
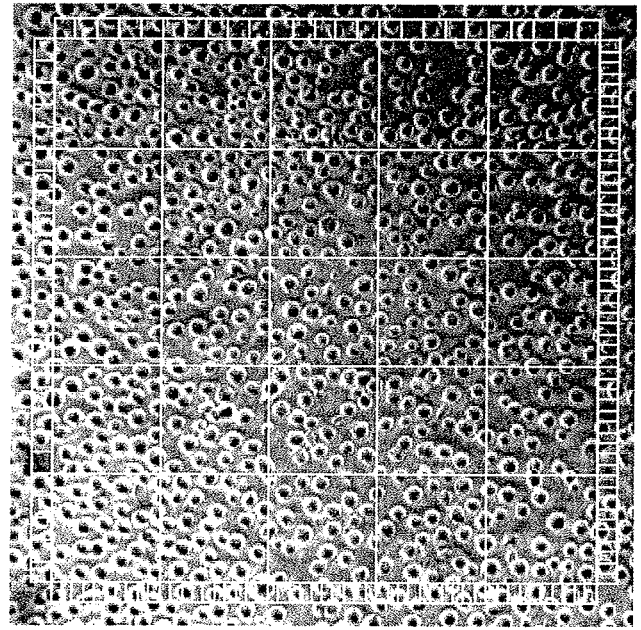
FIG. 20 shows images of cells of example 1 of the present invention and of comparative example 1.
Figure 20:
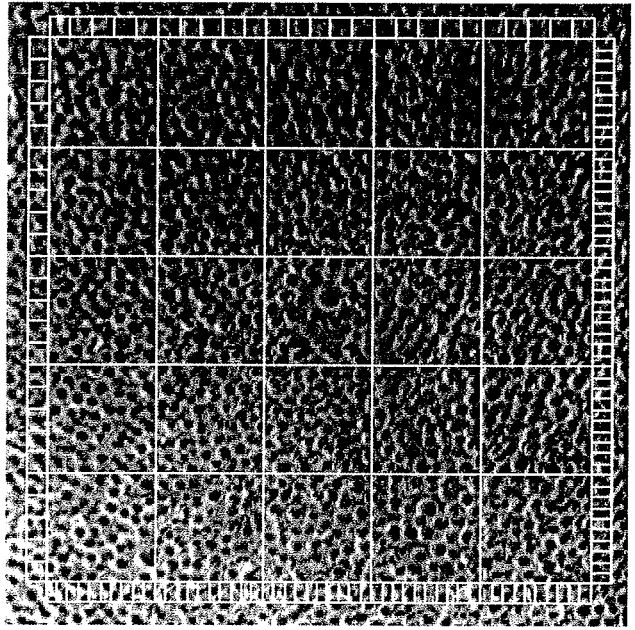

Immediately after the agitation, a thickness adjusting member made of an acrylic board with a width of 50 mm, a thickness of 3 mm, and a length longer than the longer side of the culture container 11 moved downward onto the bag to adjust the thickness of the bag to 3.1 mm. Then, the bag was kept stationary for 12 minutes, and then the observation region was photographed, followed by counting of the number of the cells. Then, the cell density was calculated based on the obtained cell number and the volume of the observation region. FIG. 20 shows a photographed image, and FIG. 21 shows the number of the cells in the observation region, the cell density, an actual measurement density, and an actual measurement ratio.

The actual measurement density was obtained such that the number of the cells in the culture solution collected from the bag was measured using a counter board (OneCell counter (available from OneCell Corporation)) according to a conventional method, and the measured number was divided by the volume of the observation region.

Comparative Example 1

The agitation was carried out under the same agitating conditions with the same culture container 11 and the culture solution as those in example 1.

Next, after the bag was kept stationary for 60 minutes without being adjusted in thickness, the observation region was photographed. Since the upper face of the bag was not pressed, its upper surface was in the form of a convexoconcave wave. The thickness of the bag was approximately 16 mm.

In this case, overlapping was observed among the cells, which made it impossible to count the number of the cells and thus impossible to calculate the density. The results are shown in FIG. 20 and FIG. 21.

Example 2

Figure 22:
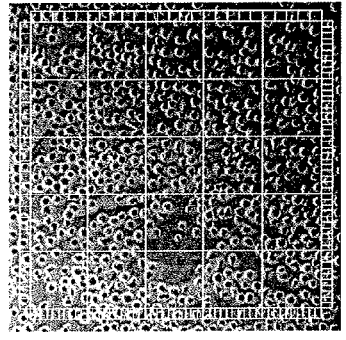
FIG. 22 is a diagram showing images of cells in examples 2 to 5 of the present invention.
Figure 22:
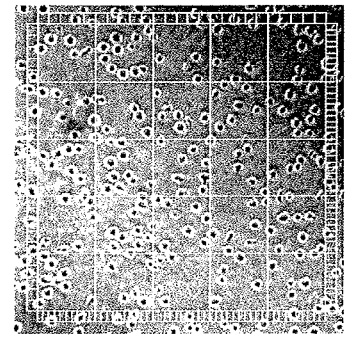
Figure 22:
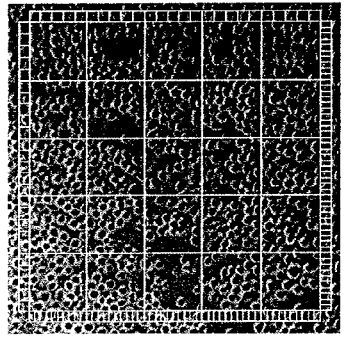
Figure 22:
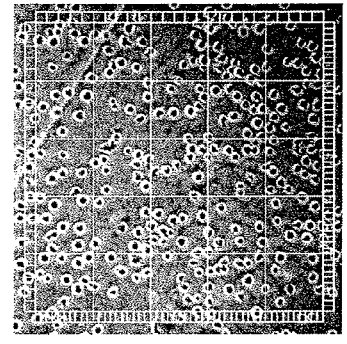
Figure 24:
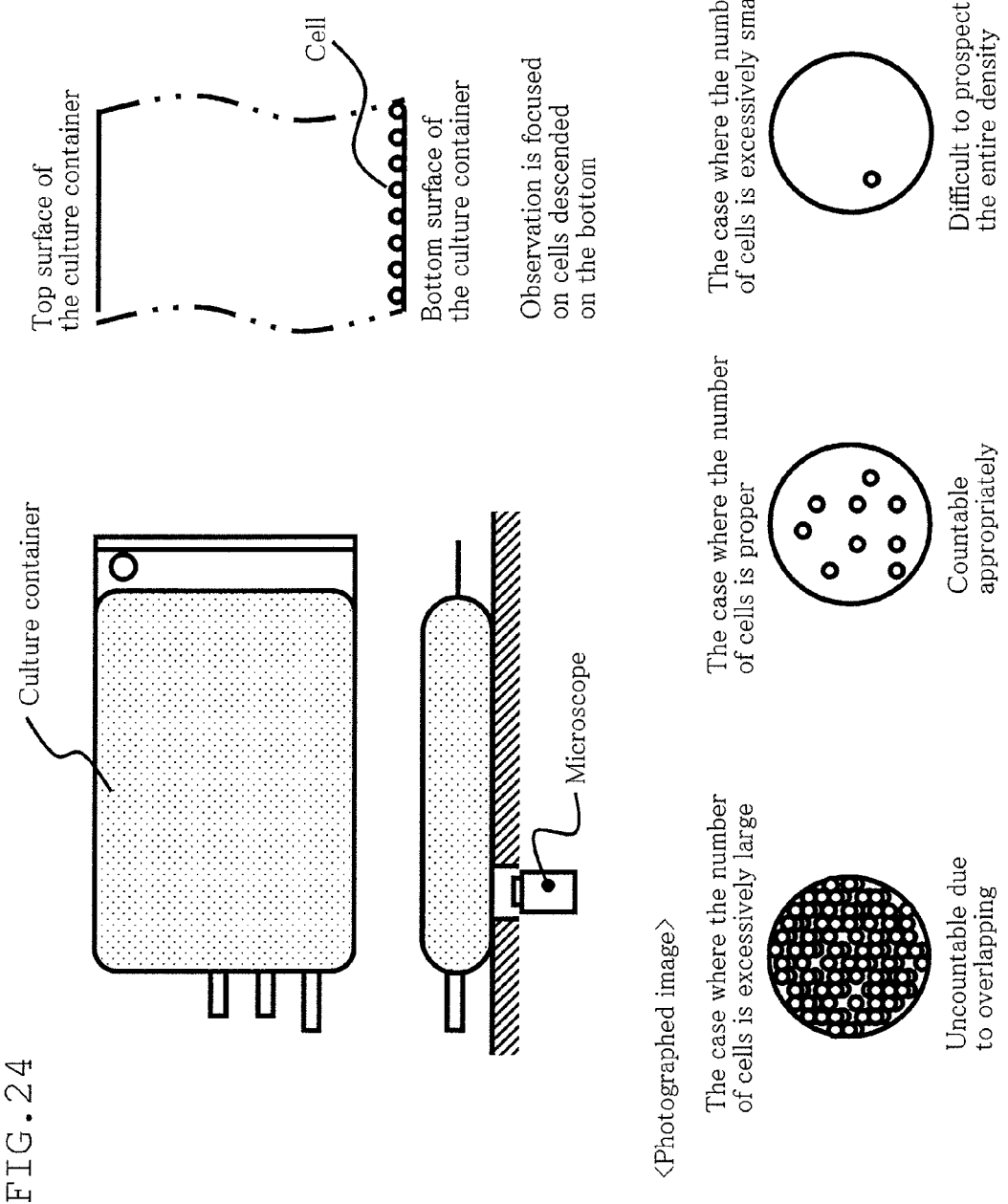
FIG. 24 is a diagram showing a conventional method for counting counted targets disposed in a container.

Example 2 was carried out in the same manner as in example 1 except that the culture solution used had a different cell density from the cell density in example 1; the thickness of the bag was 11.0 mm in the counting of the number of the cells; and the period of time for keeping the bag stationary after the adjustment of the thickness was 45 minutes. The kind of the culture solution and the kind of the cultured cells were the same as those in example 1. The number of the cells used in this example was smaller than that in example 1. The results are shown in FIG. 22 and FIG. 23.

Example 3

Example 3 was carried out in the same manner as in example 2 except that in the measurement of the number of the cells, the thickness of the bag was 7.0 mm, and the period of time for stationary keeping thereafter was 30 minutes. The results are shown in FIG. 22 and FIG. 23.

Example 4

Example 4 was carried out in the same manner as in example 2 except that in the measurement of the number of the cells, the thickness of the bag was 4.0 mm, and the period of time for stationary keeping thereafter was 12 minutes. The results are shown in FIG. 22 and FIG. 23.

Example 5

Example 5 was carried out in the same manner as in example 2 except that in the measurement of the number of the cells, the thickness of the bag was 3.1 mm, and the period of time for stationary keeping thereafter was 12 minutes. The results are shown in FIG. 22 and FIG. 23.

As shown in FIG. 20 and FIG. 21, in comparative example 1, in which the thickness of the bag was not adjusted, the cells overlapped with each other and the counting of the cell number was inaccurate. Examples of the impossibility of counting include the case where the result of the number counting is equal to or more than a predetermined value (the maximum number of cells viewable in the observation region), in addition to the case where the number cannot be actually calculated.

In contrast, in example 1, reducing the thickness of the bag ensured measurement of the number of the cells, and ensured calculation of the density of the cells disposed in the culture container 11.

Also FIG. 22 and FIG. 23 show that in Examples 2 through 5, as the thickness of the bag reduces, the measured number of the cells lowers. It is also shown that the calculated cell densities are not significantly different from the corresponding actual measurement densities.

Thus, it has been found that when the number of the cells is excessively large for number counting, as the density of the cells is larger, reducing the thickness of the bag to a larger degree ensures measurement of the cells.

These experimental results clearly show that with the method for counting counted targets disposed in a container using the counting apparatus according to the embodiment of the present invention, the number of cells in a culture container is measured and the density of cells is calculated without disassembly of the culture system and irrespective of the density of cells.

The present invention is not limited to the above embodiments, and it will be appreciated that various changes and modifications may be made within the scope of the present invention.

As examples of changes and modifications, the culture container 11 may be rounded to eliminate corners, and the agitating member 14 may have other than a columnar shape and may have the cross section shown in FIG. 17 formed into various cross sections such as a star, so as to obtain various agitation effects.

While in the above-described embodiments and examples the cultured cells are the measurement target, this should not be construed in a limiting sense. For example, the measurement target may be other organisms such as plankton and inorganic substances. Examples of the "liquid" in the culture container include semi-liquids in addition to liquids such as a culture solution. It is also possible to use a liquid having a specific gravity larger than the specific gravity of the cultured cells as a culture solution in the culture container 11. This makes the cultured cells located at the upper portion in the culture container 11, and the number counting may be with respect to such cultured cells. Further, in the above-described embodiments and examples, it is also possible to observe the growth state of cells, as well as counting the number of the cells.

INDUSTRIAL APPLICABILITY

The present invention finds applications in fields that involve culturing of a large quantity of cells, such as biomedicine, regenerative medical therapy, and immunotherapy.

The invention claimed is:

1. A method for counting cells disposed in a liquid enclosed in a flexible culture container, comprising:
    pressing a part of the container from a top side or a lower side by a pressing plate as a thickness adjusting member, thereby adjusting a thickness of the container;
    setting at least a part of the container adjusted by the pressing as a measurement target region; and
    counting a number of cells in the measurement target region.

2. The method according to claim 1, further comprising, prior to adjusting the thickness of at least the part of the container, agitating the liquid in the container to equalize the cells in the liquid.

3. The method according to claim 1, further comprising, based on the counted number of the cells, calculating a density of the cells in the liquid, and/or calculating a number of cells throughout the liquid.

4. The method according to claim 1, wherein the counting step of the number of the cells comprises counting the number of the cells in a photographed image of the measurement target region.

5. The method according to claim 1, further comprising reducing the thickness of the container at a portion pressed by pressing the part of the container from the top side or the lower side by the pressing plate when the number of the cells in the measurement target region is equal to or more than a predetermined value, and then counting the number of cells.

6. The method according to claim 1, further comprising increasing the thickness of the container at a portion other than a portion pressed by pressing the part of the container from the top side or the lower side by the pressing plate when the number of the cells in the measurement target region is less than a predetermined value, and then counting the number of cells.

7. The method according to claim 1, wherein at least a part of the pressing plate located above the measurement target region of the culture container is made of a transparent material.

* * * * *